US008446280B2

(12) United States Patent
Ortenzi et al.

(10) Patent No.: US 8,446,280 B2
(45) Date of Patent: May 21, 2013

(54) SYSTEMS AND METHODS FOR MANAGING INFORMATION RELATING TO MEDICAL FLUIDS AND SYRINGES THEREFOR

(75) Inventors: Vernon D. Ortenzi, Burlington, KY (US); Chad M. Gibson, Mason, OH (US); Victor Lee Potter, Middletown, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 584 days.

(21) Appl. No.: 12/016,583

(22) Filed: Jan. 18, 2008

(65) Prior Publication Data

US 2008/0147015 A1 Jun. 19, 2008

Related U.S. Application Data

(63) Continuation-in-part of application No. PCT/US2006/012620, filed on Apr. 4, 2006.

(60) Provisional application No. 60/668,647, filed on Apr. 6, 2005, provisional application No. 60/716,166, filed on Sep. 12, 2005, provisional application No. 60/668,681, filed on Apr. 6, 2005, provisional application No. 60/681,252, filed on May 16, 2005, provisional application No. 60/718,545, filed on Sep. 19, 2005.

(51) Int. Cl.
*G08B 13/14* (2006.01)

(52) U.S. Cl.
USPC .......................................... 340/572.1; 604/19

(58) Field of Classification Search .................. 604/189, 604/500–522, 232, 131, 151, 152; 340/603, 340/572.1
See application file for complete search history.

(56) References Cited

U.S. PATENT DOCUMENTS 2,195,976 A 4/1940 Schlitt
4,296,334 A 10/1981 Wong (Continued)

FOREIGN PATENT DOCUMENTS

EP 1433456 A1 3/2004
EP 1433456 A1 6/2004

(Continued)

OTHER PUBLICATIONS

Wei et al., Integration between Hospital Information System and PACS, Jun. 2001.

*Primary Examiner* — Kevin C Sirmons
*Assistant Examiner* — Imani Hayman
(74) *Attorney, Agent, or Firm* — Marsh Fischmann & Breyfogle LLP

(57) ABSTRACT

An apparatus and method of operation is provided for a contrast media injector having a powered drive ram. The drive ram is designed to interface with a plunger of a syringe in order to move the plunger forward and backward relative to a barrel of the syringe. The syringe, having an RF data tag associated therewith, is mounted on to the contrast media injector. Electromagnetic signals are transmitted from an electromagnetic device of the injector in response to mounting the syringe. Data is electromagnetically read from the RF data tag of the syringe using the electromagnetic device of the injector. The transmitting is terminated after the electromagnetically reading. Medical fluid is then dispensed from the syringe. Electromagnetic signals are transmitted from the electromagnetic device in response to initiation of the dispensing. Data is electromagnetically written to the RF data tag of the syringe using the electromagnetic device of the injector.

33 Claims, 25 Drawing Sheets

U.S. PATENT DOCUMENTS

| | | | | |
|---|---|---|---|---|
| 4,401,108 | A | 8/1983 | Galkin et al. | |
| 4,526,404 | A | 7/1985 | Vazquez | |
| 4,604,847 | A | 8/1986 | Moulding et al. | |
| 4,690,676 | A | 9/1987 | Moulding et al. | |
| 4,781,696 | A | 11/1988 | Moulding et al. | |
| 4,853,521 | A | 8/1989 | Claeys et al. | |
| 4,854,324 | A | 8/1989 | Hirschman et al. | |
| 4,897,789 | A | 1/1990 | King et al. | |
| 4,954,969 | A | 9/1990 | Tsumura | |
| 4,978,335 | A | 12/1990 | Arthur | |
| 5,047,014 | A | 9/1991 | Mosebach et al. | |
| 5,078,683 | A | 1/1992 | Sancoff et al. | |
| 5,108,372 | A | 4/1992 | Swenson | |
| 5,195,976 | A | 3/1993 | Swenson | |
| 5,274,239 | A | 12/1993 | Lane et al. | |
| 5,306,252 | A | 4/1994 | Yutori et al. | |
| 5,317,506 | A | 5/1994 | Coutre et al. | |
| 5,322,511 | A | 6/1994 | Armbruster et al. | |
| 5,378,231 | A | 1/1995 | Johnson et al. | |
| 5,383,858 | A | 1/1995 | Reilly et al. | |
| 5,445,621 | A | 8/1995 | Poli et al. | |
| 5,568,810 | A | 10/1996 | Hamers et al. | |
| 5,651,775 | A | 7/1997 | Walker et al. | |
| 5,662,612 | A | 9/1997 | Niehoff | |
| 5,681,285 | A | 10/1997 | Ford et al. | |
| 5,699,803 | A | 12/1997 | Carodiskey | |
| 5,729,236 | A | 3/1998 | Flaxl | |
| 5,739,508 | A | 4/1998 | Uber | |
| 5,741,232 | A | 4/1998 | Reilly et al. | |
| 5,840,026 | A | 11/1998 | Uber et al. | |
| 5,865,805 | A | 2/1999 | Ziemba | |
| 5,882,338 | A | 3/1999 | Gray | |
| 5,920,054 | A | 7/1999 | Uber et al. | |
| 5,920,554 | A | 7/1999 | Nakamura et al. | |
| 5,927,351 | A | 7/1999 | Zhu et al. | |
| 5,928,197 | A * | 7/1999 | Niehoff | 604/155 |
| 5,954,700 | A | 9/1999 | Kovelman | |
| 5,980,501 | A | 11/1999 | Gray | |
| 5,997,502 | A | 12/1999 | Reilly et al. | |
| 6,019,745 | A * | 2/2000 | Gray | 604/131 |
| 6,036,458 | A | 3/2000 | Cole et al. | |
| 6,069,853 | A | 5/2000 | Novotny et al. | |
| 6,090,064 | A | 7/2000 | Reilly et al. | |
| 6,110,152 | A | 8/2000 | Kovelman | |
| 6,159,183 | A | 12/2000 | Neer et al. | |
| 6,161,031 | A | 12/2000 | Hochman et al. | |
| 6,167,394 | A | 12/2000 | Leung | |
| 6,221,051 | B1 | 4/2001 | Hjertman et al. | |
| 6,269,340 | B1 | 7/2001 | Ford et al. | |
| 6,269,648 | B1 | 8/2001 | Hasson et al. | |
| 6,344,030 | B1 | 2/2002 | Duchon et al. | |
| 6,351,215 | B2 | 2/2002 | Rodgers et al. | |
| 6,366,206 | B1 | 4/2002 | Ishikawa et al. | |
| 6,385,483 | B1 | 5/2002 | Uber, III et al. | |
| 6,387,092 | B1 | 5/2002 | Burnside et al. | |
| 6,397,098 | B1 | 5/2002 | Uber, III et al. | |
| 6,397,334 | B1 | 5/2002 | Chainer et al. | |
| 6,402,717 | B1 | 6/2002 | Reilly et al. | |
| 6,440,158 | B1 | 8/2002 | Saab | |
| 6,475,192 | B1 | 11/2002 | Reilly et al. | |
| 6,536,456 | B2 | 3/2003 | Dickerson, Jr. et al. | |
| 6,575,906 | B1 | 6/2003 | Schembri, Jr. et al. | |
| RE38,189 | E | 7/2003 | Walker et al. | |
| 6,626,862 | B1 | 9/2003 | Duchon et al. | |
| 6,633,513 | B1 | 10/2003 | Kim et al. | |
| 6,641,052 | B2 | 11/2003 | Baillod et al. | |
| 6,685,678 | B2 | 2/2004 | Evans et al. | |
| 6,704,592 | B1 | 3/2004 | Reynolds et al. | |
| 6,714,121 | B1 | 3/2004 | Moore | |
| 6,733,478 | B2 | 5/2004 | Reilly et al. | |
| 6,733,495 | B1 | 5/2004 | Bek et al. | |
| 6,743,202 | B2 | 6/2004 | Hirschman et al. | |
| 6,751,615 | B2 | 6/2004 | Nisler | |
| 6,808,513 | B2 | 10/2004 | Reilly et al. | |
| 6,828,577 | B2 | 12/2004 | Zens | |
| 6,846,298 | B1 | 1/2005 | Carr et al. | |
| 6,861,954 | B2 | 3/2005 | Levin | |
| 6,861,993 | B2 | 3/2005 | Waldner | |
| 6,901,283 | B2 | 5/2005 | Evans, III et al. | |
| 6,903,656 | B1 | 6/2005 | Lee | |
| 6,920,088 | B2 | 7/2005 | Wickramasinghe et al. | |
| 6,958,053 | B1 | 10/2005 | Reilly | |
| 6,961,000 | B2 | 11/2005 | Chung | |
| 6,962,601 | B2 | 11/2005 | Becker et al. | |
| 6,980,419 | B2 | 12/2005 | Smith et al. | |
| 6,995,641 | B2 | 2/2006 | Hasson et al. | |
| 6,995,673 | B1 | 2/2006 | Osredkar | |
| 7,012,529 | B2 | 3/2006 | Sajkowsky | |
| 7,034,683 | B2 | 4/2006 | Ghazarian | |
| 7,158,030 | B2 | 1/2007 | Chung | |
| 7,171,426 | B2 | 1/2007 | Farmer et al. | |
| 7,175,081 | B2 | 2/2007 | Andreasson et al. | |
| 7,258,276 | B2 | 8/2007 | Linton et al. | |
| 7,264,148 | B2 | 9/2007 | Tachibana | |
| 7,299,981 | B2 | 11/2007 | Hickle et al. | |
| 7,304,913 | B2 | 12/2007 | Niemiec | |
| 7,366,675 | B1 | 4/2008 | Walker et al. | |
| 2001/0028308 | A1 | 10/2001 | De La Huerga | |
| 2001/0034506 | A1 | 10/2001 | Hirschman et al. | |
| 2002/0020444 | A1 | 2/2002 | Dickerson, Jr. et al. | |
| 2002/0038392 | A1 | 3/2002 | De La Huerga | |
| 2002/0044059 | A1 | 4/2002 | Reeder | |
| 2002/0076429 | A1 | 6/2002 | Wironen et al. | |
| 2002/0106411 | A1 | 8/2002 | Wironen et al. | |
| 2002/0111584 | A1 | 8/2002 | Walker et al. | |
| 2002/0112636 | A1 | 8/2002 | Desaulniers et al. | |
| 2002/0118111 | A1 | 8/2002 | Brown | |
| 2002/0143320 | A1 | 10/2002 | Levin | |
| 2002/0176893 | A1 | 11/2002 | Wironen et al. | |
| 2002/0180606 | A1 | 12/2002 | Kitaguchi | |
| 2002/0188259 | A1 | 12/2002 | Hickle | |
| 2002/0196150 | A1 | 12/2002 | Wildman | |
| 2003/0006878 | A1 | 1/2003 | Chung | |
| 2003/0011476 | A1 | 1/2003 | Godfrey | |
| 2003/0040700 | A1 | 2/2003 | Hickle et al. | |
| 2003/0052788 | A1 | 3/2003 | Chung | |
| 2003/0055685 | A1 | 3/2003 | Cobb | |
| 2003/0060754 | A1 | 3/2003 | Reilly | |
| 2003/0060761 | A1 | 3/2003 | Evans et al. | |
| 2003/0074223 | A1 | 4/2003 | Hickle | |
| 2003/0092956 | A1 | 5/2003 | Williams | |
| 2003/0125665 | A1 | 7/2003 | Rosenman | |
| 2003/0135388 | A1 | 7/2003 | Martucci et al. | |
| 2003/0139640 | A1 | 7/2003 | Whittacre et al. | |
| 2003/0152519 | A1 | 8/2003 | Koenig et al. | |
| 2003/0160698 | A1 | 8/2003 | Andreasson et al. | |
| 2003/0174046 | A1 | 9/2003 | Abrams | |
| 2003/0183226 | A1 | 10/2003 | Brand et al. | |
| 2003/0183683 | A1 | 10/2003 | Stewart | |
| 2003/0216688 | A1 | 11/2003 | M.A.J.M. et al. | |
| 2003/0233069 | A1 | 12/2003 | Gillespie et al. | |
| 2004/0008123 | A1 | 1/2004 | Carrender et al. | |
| 2004/0019464 | A1 | 1/2004 | Martucci et al. | |
| 2004/0024361 | A1 | 2/2004 | Fago et al. | |
| 2004/0027244 | A9 | 2/2004 | Menard | |
| 2004/0049422 | A1 | 3/2004 | Mortimer | |
| 2004/0051368 | A1 | 3/2004 | Caputo et al. | |
| 2004/0054325 | A1 | 3/2004 | Ginsburg | |
| 2004/0100376 | A1 | 5/2004 | Lye | |
| 2004/0104271 | A1 | 6/2004 | Martucci et al. | |
| 2004/0176984 | A1 | 9/2004 | White | |
| 2004/0193449 | A1 | 9/2004 | Wildman | |
| 2004/0199075 | A1 | 10/2004 | Evans, III et al. | |
| 2004/0199076 | A1 | 10/2004 | Nemoto | |
| 2004/0199115 | A1 | 10/2004 | Rosenman | |
| 2004/0220824 | A1 | 11/2004 | Imai | |
| 2005/0029277 | A1 | 2/2005 | Tachibana | |
| 2005/0035862 | A1 | 2/2005 | Wildman | |
| 2005/0038386 | A1 | 2/2005 | Fago et al. | |
| 2005/0049556 | A1 | 3/2005 | Tanaka | |
| 2005/0104363 | A1 | 5/2005 | Wright et al. | |
| 2005/0107698 | A1 | 5/2005 | Powers et al. | |
| 2005/0182358 | A1 | 8/2005 | Veit et al. | |
| 2005/0198800 | A1 | 9/2005 | Reich | |
| 2005/0277833 | A1 | 12/2005 | Williams, Jr. | |
| 2006/0030773 | A1 | 2/2006 | Uber, III et al. | |
| 2006/0072030 | A1 | 4/2006 | Silverbrook | |

2006/0089858 A1 4/2006 Ling
2006/0109105 A1 5/2006 Varner
2006/0152367 A1 7/2006 Narayanaswamy
2006/0183912 A1 8/2006 Assaf et al.
2006/0183913 A1 8/2006 Assaf et al.
2006/0187050 A1 8/2006 Wagner
2006/0211989 A1 9/2006 Rhinehart et al.
2007/0003593 A1 1/2007 Wironen et al.
2007/0021382 A1 1/2007 Assaf et al.
2007/0163583 A1 7/2007 Brand et al.
2007/0167919 A1 7/2007 Nemoto et al.
2007/0189026 A1 8/2007 Chemel et al.
2007/0191690 A1 8/2007 Hasse et al.
2007/0197974 A1 8/2007 Gibson
2007/0198297 A1 8/2007 Perkins et al.
2007/0208308 A1 9/2007 Gibson et al.
2007/0208445 A1 9/2007 Gibson et al.
2007/0225672 A1 9/2007 Wagner
2007/0272746 A1 11/2007 Ortiz et al.
2008/0045901 A1 * 2/2008 Nemoto et al. ............... 604/131
2008/0195249 A1 8/2008 Rousso

FOREIGN PATENT DOCUMENTS

EP 1723977 A1 11/2006
WO 03026724 A1 4/2003
WO 2005010796 A2 7/2004
WO 2004086997 A1 10/2004
WO 2004088567 A2 10/2004
WO 2004095379 A2 11/2004
WO 2005010796 A2 2/2005

* cited by examiner

SYSTEMS AND METHODS FOR MANAGING INFORMATION RELATING TO MEDICAL FLUIDS AND SYRINGES THEREFOR

CROSS REFERENCE TO RELATED APPLICATIONS

This application is a continuation-in-part of previously filed PCT Application PCT/US2006/012620, filed Apr. 4, 2006, entitled SYSTEMS AND METHODS FOR MANAGING INFORMATION RELATING TO MEDICAL FLUIDS AND CONTAINERS THEREFOR, the entire content of which is hereby incorporated by reference, which claims the benefit of the following U.S. Provisional Applications that are hereby incorporated in their entireties by reference herein:

U.S. Provisional Application Ser. No. 60/668,647, filed 6 Apr. 2005 and entitled SYSTEM AND METHOD FOR TRACKING INFORMATION RELATING TO A PHARMACEUTICAL CONTAINER AND/OR PHARMACEUTICAL DISPOSED THEREIN;

U.S. Provisional Application Ser. No. 60/716,166, filed 12 Sep. 2005 and entitled SYSTEM AND METHOD OF TRACKING INFORMATION RELATING TO A PHARMACEUTICAL CONTAINER IN A CT SCANNING SUITE;

U.S. Provisional Application Ser. No. 60/668,681, filed 6 Apr. 2005 and entitled APPARATUS AND METHOD FOR LABELING RADIOPHARMACEUTICALS;

U.S. Provisional Application Ser. No. 60/681,252, filed 16 May 2005 and entitled APPARATUS AND METHOD FOR LABELING RADIOPHARMACEUTICALS; and U.S. Provisional Application Ser. No. 60/718,545, filed 19 Sep. 2005 and entitled ANTENNA SYSTEM AND METHOD OF READING A DATA TAG ON A CONTRAST MEDIA CONTAINER.

FIELD OF THE INVENTION

The present invention relates generally to medical fluids (e.g., radiopharmaceuticals, contrast media) and, more particularly, to tracking and/or managing information relating to medical fluids, containers therefor, and/or medical fluid administration devices used to administer such medical fluids.

BACKGROUND

Proper administration of medical fluids (e.g., contrast media, radiopharmaceuticals) is dependent on human reliability to insure the correct drug is administered properly. In the case of injectable medical fluids, the consequences of mistakes can be severe. Statistically the accuracy of the health care system in providing correct injections is excellent. However, with millions of injections per year, there is a continuing effort to further reduce mistakes, a great majority of which are the result of human error.

Of particular interest is the packaging, distribution and use of contrast media or a contrast agent. As used herein, a contrast media or agent is a substance that is introduced into, on, or around a physiological structure (e.g., tissue, vasculature, cell); and because of the differences in absorption by the contrast media and the surrounding tissues, the contrast media allows a radiographic visualization of the structure. Contrast media is used in x-ray computed tomography (CT), magnetic resonance imaging (MR), ultrasound imaging, angiographic imaging, and other procedures. Often, a container, for example, a syringe, is filled with a desired quantity of the contrast media by an independent supplier; and the filled syringes of contrast media are sold or otherwise provided to a hospital, imaging service provider or other health care facility.

Over the useful life of the contrast media and its associated syringe, there are three principal areas of interest for tracking purposes: 1) the location where the contrast media is packaged in a container (e.g., a syringe); 2) the distribution and storage of the filled syringe; and 3) the use and disposal of the syringe. The filling of a syringe with contrast media can occur at a supplier's facility separate from a health care facility; or in some circumstances, within a pharmacy of the health care facility. Contrast media comes in many types and concentrations and can be filled in syringes of different sizes that also vary with the type of injector to be used. Further, the contrast media has a limited shelf life and a more limited life when open to atmosphere or when heated in preparation for injection. Thus, in order to properly fill a syringe with contrast media, knowledge of the contrast media's use, the injector and sometimes an identity of a patient are required. In addition, proper use of the contrast media requires knowledge of its age and other information relating to when the syringe was filled.

Currently, all this information is manually collected by pharmacists and X-ray technologists. The information pertaining to the syringes can be located on the syringe package and the syringe label, while information regarding the contrast concentration, volume, lot number, and expiration data is generally recorded in the patient's record. The technologist then uses this information, from multiple sources, to manually set up the injection; and currently, this information must be manually transposed onto various records. Known systems for managing pharmaceuticals provide filed syringes with bar codes having SKUs and other indicia relating to various filled sizes and concentrations of contrast media. But this system is limited in use and does not provide an efficient management of all of the parameters needed in a medical environment and particularly in connection with the use of contrast media. There is a need for a more automated system for entering information relating to contrast media upon filling a syringe. There is a further need to automatically track a particular syringe through a distribution system whether from a supplier external to a health care facility and/or from a pharmacy within the facility.

Power injectors are frequently used to inject X-ray contrast media into patients receiving X-ray imaging procedures. X-ray technologists may encounter distractions in the course of executing an X-ray procedure thus leading to the possibility of injecting a patient using an empty syringe. An empty syringe injection often occurs when a technologist retracts a plunger of a syringe with the power injector after an injection but inadvertently does not replace the empty syringe with a new full syringe—when the next patient is prepared for imaging the technologist fails to recognize the empty syringe loaded in the power injector because the fully retracted empty syringe looks like a full syringe with contrast media. To reduce the risk of using an empty syringe, power injectors often prompt the technologist with a message asking the technologist to confirm that air has been purged out of the syringe and tubing. However, a technologist may answer "yes" to the prompt without carefully checking the syringe and tubing with the result that air is injected into a patient. Therefore, there is a need for a more automated system for preventing use of an empty syringe.

It is possible to refill almost any empty syringe with contrast media. Some syringes are intended to be refilled, whereas others are not. However, some engage in a practice of refilling syringes that are not intended to be refilled and/or refill a syringe improperly with a risk of trapping air within the syringe. Therefore, there is a need for an automated system for tracking the use of a syringe and preventing its subsequent unauthorized re-use.

The installed base of power injectors in the world is very large due to their reliability and long useful life. Throughout the life of a power injector, the diameter and length of syringes used in that injector may vary due to tooling, material or process changes over time, or even normal variations from batch-to-batch. Known power injectors have fixed programming for syringe sizes and are not setup to automatically make adjustments for minor variations in the diameter and length of a syringe. By assuming a diameter and length for a syringe, the volume delivery accuracy of a power injector is limited. For example, variations in syringe size result in a typical volume accuracy specification for a power injector of about +/−2 milliliters ("ml") per injection, even though the electronics and mechanical transmission are capable of much better. Therefore, there is a need for an automated system for determining variations in syringe size, so that better volume delivery accuracy can be achieved.

There is also a need for an automated system that tracks syringes from the time they are filled with a contrast media, through their distribution to a health care facility and/or an imaging suite, through the injection of the contrast media from the syringe and then the disposal or authorized refilling of the syringe. There is a further need for such an automated system to communicate information regarding the injection of contrast media to patient records.

SUMMARY

The present invention is generally directed to managing information relating to a medical fluid, a container therefor, and/or a medical fluid administration device. Containers of the invention typically have a data tag associated therewith to enable information to be read from and/or written to the data tag of the container. This allows information regarding the container and/or the medical fluid associated therewith to be ascertained, and optionally updated, for example, during and/or between various stages of manufacture, transport, storage, use, and/or disposal.

As used herein, a "medical fluid" generally refers to a fluid that is designed to be administered (e.g., intravenously) to a medical patient as a part of a medical procedure (e.g., diagnostic procedure, therapeutic procedure). Examples of medical fluids include, but are not limited to, contrast media, radiopharmaceuticals, and saline. A "container" of the invention generally refers to any container designed to have a medical fluid disposed therein. Examples of containers of the invention include, but are not limited to, syringes, IV bags, and bulk contrast media containers. An "administration device" of the invention refers to any electronic device designed to at least assist in transferring medical fluid from a container to a patient. Examples of medical fluid administration devices of the invention include, but are not limited to, infusion pumps and powered contrast media injectors.

Three aspects of the invention are directed to methods of operation for a contrast media injector that has a powered drive ram designed to interface with a plunger of a syringe to move the plunger of the syringe forward and backward relative to a barrel of the syringe when the syringe is mounted on the contrast media injector. These three aspects are the first, second, and third aspects discussed below.

In the method of a first aspect of the invention, a syringe having an RF data tag associated therewith is mounted on the contrast media injector. Electromagnetic signals are transmitted from an electromagnetic device of the contrast media injector in response to the syringe being mounted on the contrast media injector. In some embodiments, initiation of this transmission of electromagnetic signals may occur substantially simultaneously with the syringe being mounted on the contrast media injector. Data is electromagnetically read from the RF data tag of the syringe in response to the syringe being mounted on the contrast media injector. The data that is electromagnetically read may be any appropriate data. For instance, in some embodiments, the data may include any of the following: syringe identification; a serial number; a use indicator of the syringe; a syringe security code; information relating to syringe volume; information relating to syringe volume delivery; syringe volume; syringe dimension information; medical fluid type; medical fluid concentration data; batch and lot numbers; shelf life data; fill date; and combinations thereof.

With regard to the first aspect of the invention, the contrast media injector may include a latch for securing the syringe that is being mounted on the contrast media injector. In such embodiments, the transmitting of electromagnetic signals may occur in response to the latch securing the syringe being mounted on the contrast media injector. In some of these embodiments, initiation of the transmitting of the electromagnetic signals may occur substantially simultaneously with the latch securing the syringe being mounted on the contrast media injector.

In the method of the second aspect of the invention, medical fluid is dispensed from a syringe having an RF data tag associated therewith. Electromagnetic signals are transmitted from an electromagnetic device of the contrast media injector in response to initiation of the dispensing of the medical fluid from the syringe. In some embodiments, initiation of this transmission of electromagnetic signals may occur substantially simultaneously with the initiation of the dispensing of the medical fluid from the syringe. Data is electromagnetically written to the RF data tag of the syringe using the electromagnetic device of the contrast media injector. The data that is electromagnetically written to the data tag may be any appropriate data. For instance, in some embodiments, the data may include any of the: time that the dispensing was finished; date that the dispensing was finished; dispensed volume; achieved flow rate; target flow rate; volume of medical fluid remaining in the syringe; dispensing time; patient name; patient weight; patient age; patient ID number; injector serial number; injector firmware version; procedure number; procedure name; technologist name; technologist identification number; hospital name; hospital identification number; imaging apparatus information; and combinations thereof.

In the method of the third aspect of the invention, a syringe having an RF data tag associated therewith is mounted on the contrast media injector. Electromagnetic signals are transmitted from an electromagnetic device of the contrast media injector in response to the syringe being mounted on the contrast media injector. Data is electromagnetically read from the RF data tag of the syringe using the electromagnetic device of the contrast media injector. The transmitting of electromagnetic signals is terminated after the data from the RF data tag is electromagnetically read. Then, medical fluid is dispensed from the syringe using the contrast media injector. Electromagnetic signals are transmitted from the electromagnetic device again; but this time, in response to initiation of the dispensing of the medical fluid from the syringe. Data is electromagnetically written to the RF data tag of the syringe using the electromagnetic device of the contrast media injector.

A fourth aspect of the invention is directed to a contrast media injector for supporting a syringe from which medical fluid is to be dispensed. The syringe includes an RF data tag for storing data that is electromagnetically readable therefrom and/or electromagnetically writable thereto. The contrast media injector includes both a powerhead and an injector control. The powerhead is operable to dispense medical fluid from the syringe and includes a drive ram designed to interface with the plunger of the syringe to move the plunger of the syringe forward and backward relative to a barrel of the syringe when the syringe is mounted on the contrast media injector. In addition, the powerhead includes an electromagnetic device designed to read data from and/or write data to the RF data tag of the syringe. The injector control is operatively connected to the powerhead and in electrical communication with the electromagnetic device. In this regard, the injector control is operable to initiate transmission of electromagnetic signals by the electromagnetic device of the powerhead to electromagnetically read data from the RF data tag of the syringe when the syringe is mounted on to the contrast media injector. Further, the injector control is operable to initiate transmission of electromagnetic signals by the electromagnetic device to electromagnetically write data to the RF data tag of the syringe when medical fluid is dispensed by the powerhead.

Various refinements exist of the features noted in relation to the above-mentioned aspects of the present invention. Further features may also be incorporated in the above-mentioned aspects of the present invention as well. These refinements and additional features may exist individually or in any combination. For instance, various features discussed herein in relation to any of the exemplary embodiments of the present invention may be incorporated into any of the aspects of the present invention alone or in any combination.

BRIEF DESCRIPTION OF THE FIGURES

The accompanying figures, which are incorporated herein and constitute a part of this specification, illustrate exemplary embodiments of the invention and, together with a general description of aspects of the invention given above, and the detailed description of various exemplary embodiments given below, serve to explain various principles of the invention.

DETAILED DESCRIPTION OF EXEMPLARY EMBODIMENTS

Figure 1A:
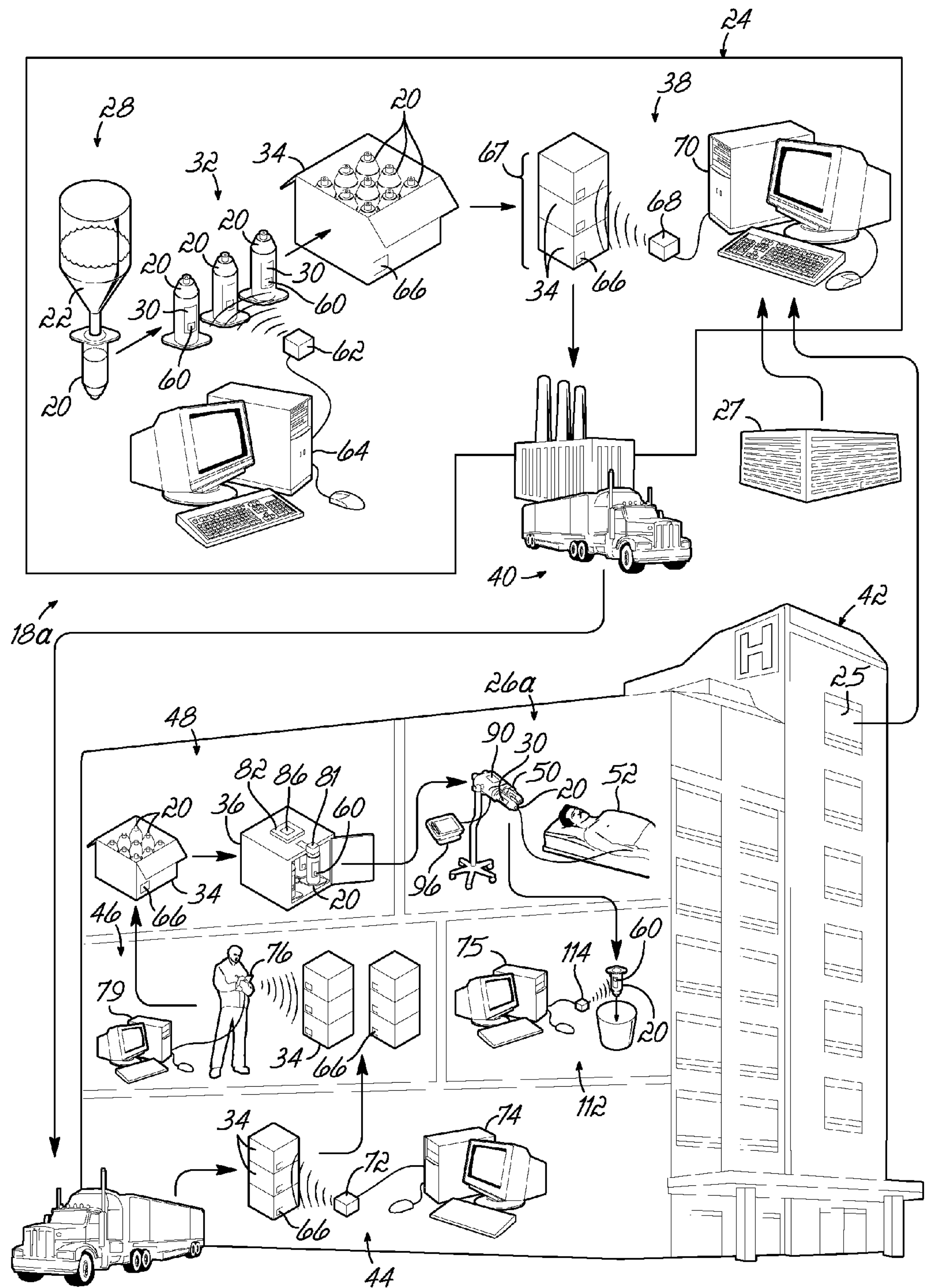
FIG. 1A is a schematic drawing of a system for tracking a syringe filled with contrast media over a syringe life cycle.

Referring to FIG. 1A, an exemplary embodiment of a container life cycle 18*a* relates to medical fluid containers, for example, a syringe 20 suitable for storing contrast media. The syringes 20 may be manufactured at a supplier facility 24 that is remote from a facility 42 in which a syringe 20 is to be used. Within the supplier facility 24, the syringe 20 is first filled with a contrast media at a filling station 28, and thereafter, labels 30 may be applied to respective syringes 20 at a labeling station 32. The syringes 20 may then be packaged either singularly or as a batch in an appropriate shipping carton 34 at a packaging station and the shipping cartons 34 may be temporarily queued or stored in a shipping/receiving department 38.

Orders for the syringes 20 can be received from various sources, for example, a purchasing office 25 within a health care facility 42, or a doctor's office 27 that may be part of, or independent from, the health care facility 42. Further, the orders may or may not be associated with a particular patient.

Based on the orders, the shipping cartons 34 may enter a distribution channel 40 by which they may be delivered to various facilities 42, for example, hospitals, image service providers, and/or other health care facilities. In the example of FIG. 1A, the facility 42 is a hospital that has a shipping/receiving area 44 for receiving the cartons 34 of prefilled syringes 20. Incidentally, "prefilled" herein describes a container that is designed to be sold and/or delivered to a user with at least some medical fluid already disposed in the container. Often, the cartons 34 are temporarily stored in a room 46 that may or may not be associated with a pharmacy within the hospital 42. As desired, the cartons 34 may be transferred to a preparation room 48 at which the syringes 20 may be unpacked and placed in a warming oven 36 to raise the temperature of the contrast media up to about body temperature (e.g., between about 97° F. and about 100° F.). At appropriate times, one or more syringes 20 may be removed from the warming oven 36, carried to the imaging suite 26*a* and loaded into a powered fluid injector 50. The injector 50 operates to inject the contrast fluid into an examination subject or patient 52. After use, the spent syringe 20 may be processed for an authorized refilling or disposed of (e.g., in a disposal area 112) in a known manner. For purposes herein, the term "prefilled syringe" means a syringe 20 prefilled with a medical fluid (e.g., contrast media) at a location remote from the preparation room 48 and imaging suite 26*a*.

As with any substance to be injected into an animal, there are a great many regulated practices as well as unregulated common practices that are desirable to be followed in the filling, distribution, preparation and use of a prefilled syringe. Further, the regulated and common practices may differ depending on the type of contrast media being used. Consequently, it is generally desirable to generate and provide a substantial amount of data relating to the handling of the syringe 20 throughout its life cycle, for example, at substantially every step from its filling to its disposal. Further, it is generally preferred that the data be transferable from one location, for example, the respective filling and labeling stations 28, 32, to another location, for example, the respective preparation and imaging rooms 48, 26*a*. Today, such data has been known to be recorded and transferred utilizing typed and/or hand-written information located on the syringes 20 and/or cartons 34 as well as typed and/or hand-written records associated therewith. However, during the life of a syringe 20, the data is desired to be utilized in computer systems that may, most often, not be integrated and sometimes, in databases that may not be compatible.

In order to provide a common data acquisition and storage system for each syringe 20, which can be utilized during any portion, and at every stage, of the container life cycle 18*a*, a system of radio frequency identification device ("RFID") tags and readers is used.

The object of an RFID-based system is to carry data in transponders, generally known as tags, and to retrieve data, by machine-readable means, at a suitable time and place to satisfy a particular application need. Thus, a tag or transponder may typically include an RF driver circuit and associated antenna. The RF driver circuit often utilizes an integrated circuit chip having a programmable processor and associated memory, which are capable of storing the data and performing necessary demodulation and, if applicable, modulation functions. Data within a tag may provide any manner of information relating to a prefilled syringe that is useful over the life of the syringe. It is generally preferred that an RFID system include a means for reading data from, and in some applications, writing data to, the tags, as well as a means for communicating the data to a computer or information management system. Thus, an RFID system preferably has the versatility to permit data to be written into, and read from, a tag at different times and at different locations.

Wireless communication is most often used to transfer data between a tag and a reader. Such communication is often based upon propagating electromagnetic waves, for example, radio frequency waves, by antenna structures present in both tags and readers. It is known to use either a common antenna or different antennas with an RFID tag to read data from, and write data to, the tag; closed loop, open loop, stripline, dipole and/or other antennas may be used. Further, RFID tags may be passive, that is, without an independent power supply, or active, that is, with a power supply such as a battery. In applications described herein, the choice of a particular antenna configuration and whether to use an active or passive RFID tag may or may not be application dependent.

Figure 2A:
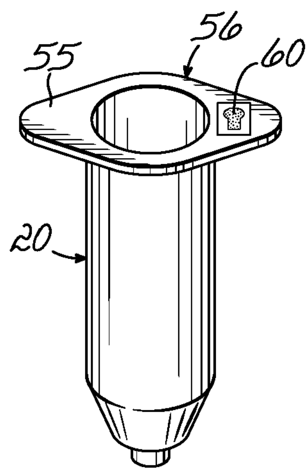
FIGS. 2A-2D are perspective views of a syringe that illustrate different manners of applying a tracking device to a syringe filled with contrast media in the system shown in FIG. 1A.
Figure 2B:
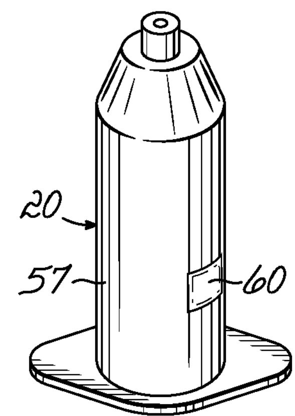
Figure 2C:
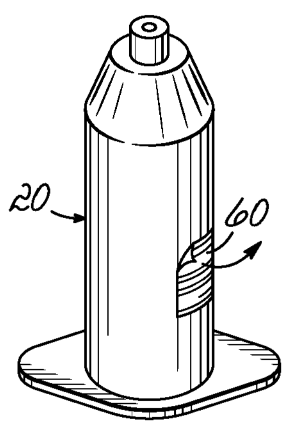
Figure 2D:
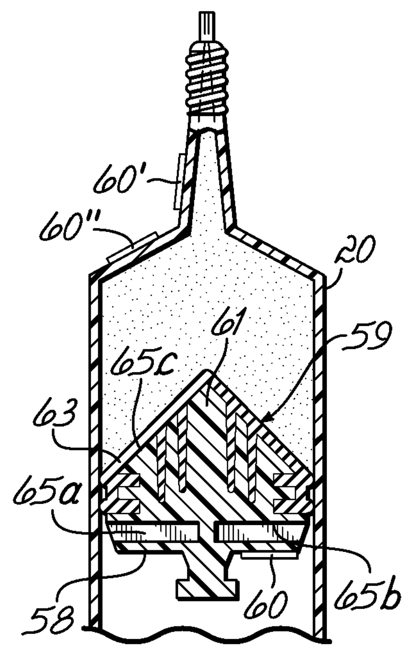
Figure 5A:
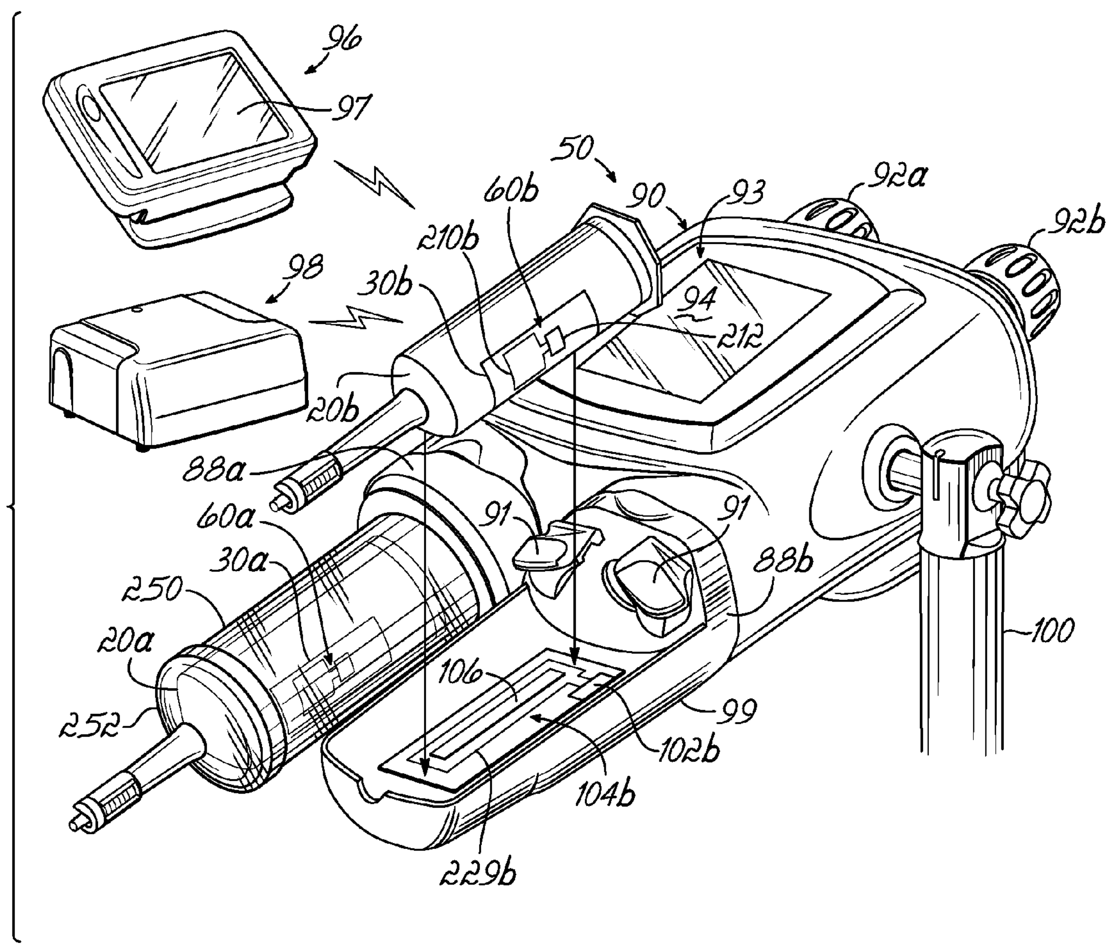
FIG. 5A is a perspective view of one embodiment of an injector that may be used in the system of FIG. 1A.
Figure 6:
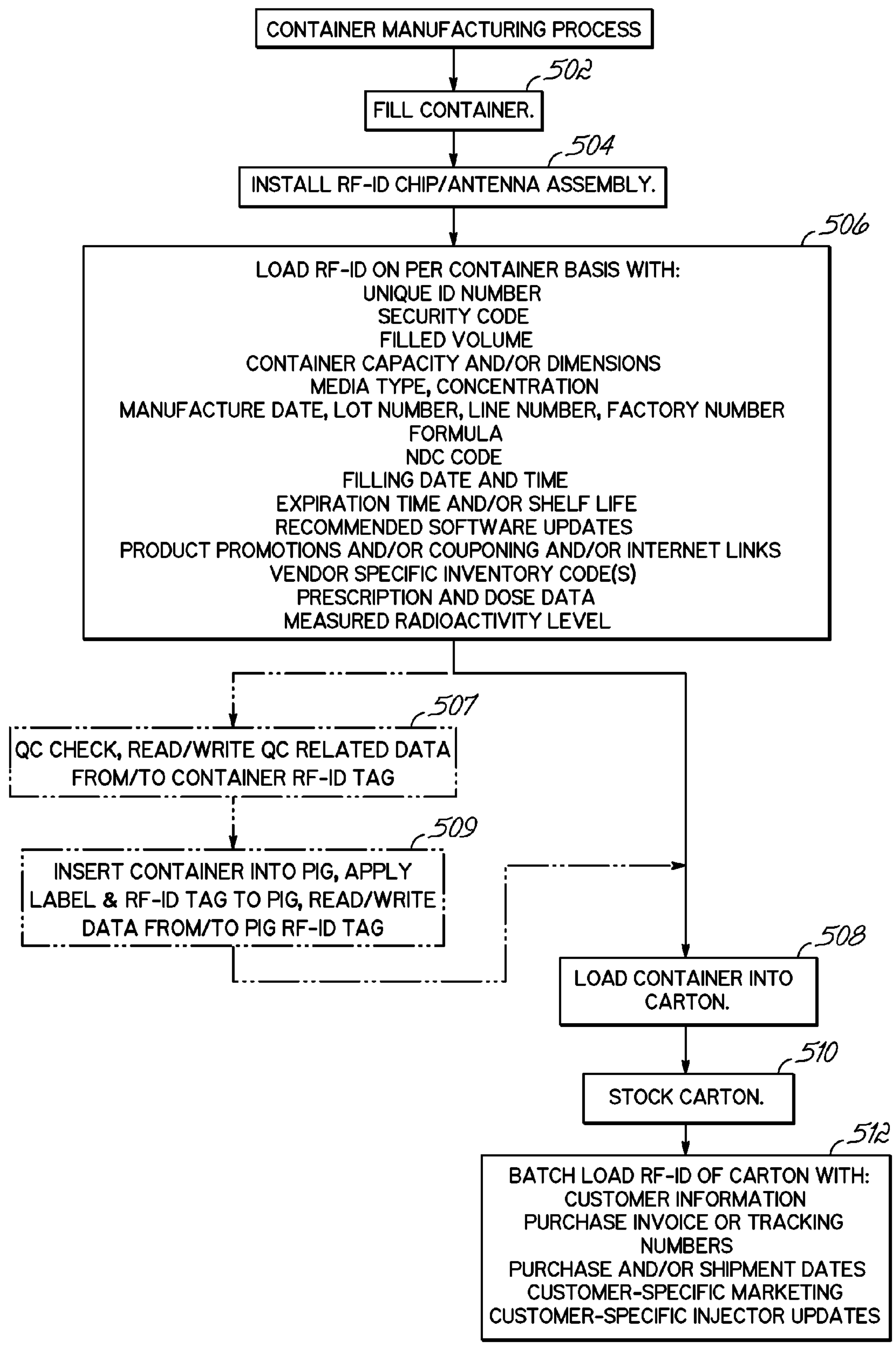
FIG. 6 is a flowchart of an exemplary method of manufacturing and distributing a syringe or other container as shown in FIGS. 1A and 1B.

An exemplary embodiment of a syringe manufacturing process implemented at a supplier facility 24 is illustrated in FIG. 6. First, at 502, a syringe 20 is filled with contrast media 22 at a filling station 28. Thereafter, at 504, a label 30 containing human readable and/or machine-readable indicia is applied to the syringe 20 at the labeling station 32. As part of the labeling process, an RFID tag 60 is applied to the syringe 20. The RFID tag 60 incorporates an RFID chip and associated antenna in a known manner, for example, as shown in FIG. 5A by the RFID chip 212 and antenna 210; and the RFID tag 60 may be a part of or separate from the label 30. As shown in FIGS. 2A-2D, the RFID tag can be applied at any suitable location on the syringe 20. For example, as shown in FIG. 2A, the RFID tag 60 can be applied to a rear surface 55 of a syringe flange 56; and as shown in FIG. 2B, the RFID tag 60 can be applied to an outer cylindrical surface 57 of the syringe. In another embodiment shown in FIG. 2C, prior to the syringe 20 being loaded into a power head of an injector, the RFID tag 60 can be peeled off of the syringe 20 and applied to the injector. Upon removing the syringe 20 from the injector power head, the RFID tag may be reapplied to the syringe 20. In a still further embodiment shown in FIG. 2D, the RFID tag 60 can be applied to a rear surface 58 of a plunger 59. The plunger 59 may have a core 61 covered by a molded material 63, and an RFID tag can be applied to or integrated into the plunger structure at various locations 65*a*, 65*b*, 65*c*, etc. As shown in FIG. 2D, an RFID tag may be applied as shown at 60' on the discharge extension (e.g., nozzle) extending from the distal end of the syringe 20, or as shown at 60", an RFID tag can be applied to a front wall (e.g., tapering front wall) of the syringe 20.

Within the supplier facility 24 of FIG. 1A, a read/write ("R/W") device 62 is connected to a labeling computer 64 and, at 506 (FIG. 6), is operative to write data in the RFID tag 60 relating to contrast media or other pharmaceutical and its associated prefilled syringe or other container 20. Data that can be written to the RFID tag 60 includes, but is not limited to, the following:

- A unique container identification number.
- A security code that limits access to the RFID tag to those R/W devices that are able to provide the security code.
- A volume of the pharmaceutical filled in the container.
- A total available volume and/or physical dimensions of the available volume in the container.
- An identity, or type, of the pharmaceutical in the container.
- A concentration of the pharmaceutical.
- A formula of the pharmaceutical.
- A manufacturing date.
- An identity of a factory, production line, filling station machine, and/or batch number associated with the container.
- A date and time at which the container is filled.
- An expiration time and/or date and/or a shelf life of the pharmaceutical.
- NDC codes.
- One or more vendor specific inventory codes, for example, an SKU code.
- An identity of the country in which the container was filled.
- An identity of the container and/or container packaging.
- Product promotions and/or coupons and/or Internet links of the supplier.
- Recommended software updates for power injectors in which the container is intended for use.

Thereafter, at 508, the syringe 20 is loaded into a shipping carton 34; and, at 510, the cartons 34 are stocked as inventory in a shipping/receiving department 38. Based on orders received, as indicated at 512, the cartons 24 may be further combined or palletized into a case or batch 67 for shipment to a customer; and a label 66 can be optionally applied to an individual shipping carton 34 or a unified case or batch 67 of cartons. The label 66 can include human readable, machine-readable indicia and/or be an RFID tag. Such indicia or RFID tag data may include but is not limited to an identification of the supplier and the product, the product expiration date and the packaging. The packaging code identifies whether the package is a single syringe, a carton of syringes or a case of syringes. In preparing one or a batch of cartons 34 for shipment, an R/W device 68 connected to a shipping computer 70 may be used to read data from, and write data to, the RFID tags 60 on the syringes 20 within the cartons 34. In addition, if applicable, the R/W device 68 may be used to read data from, and write data to, RFID tags associated with the labels 66. Thus, the shipping computer 70 is able to identify parameters, for example, type of syringe, type of contrast media, contrast media concentration, etc., and confirm that those parameters meet the specifications of a particular order. Thus, the R/W device 68 can be used to write into either the RFID tags 60 on the syringes 20, and/or the RFID tags on labels 66, data including, but not limited to, the following:

- An identity of the customer.
- Purchase invoice and tracking numbers.
- Purchase and/or shipment dates.
- Customer specific marketing data.
- Customer specific software updates for power injectors owned by the customer.

Figure 3A:
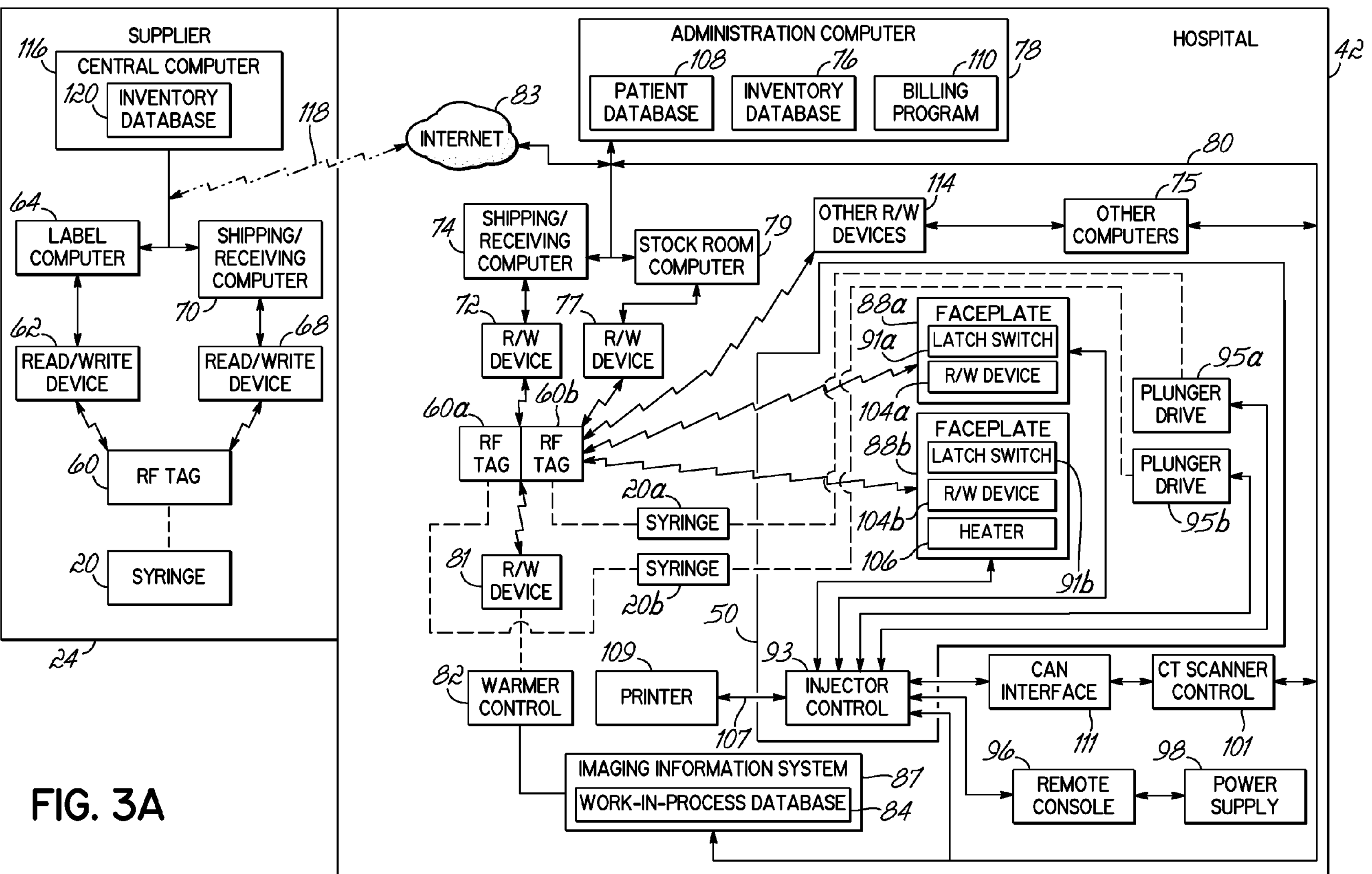
FIG. 3A is a schematic block diagram of components associated with the system illustrated in FIG. 1A.
Figure 7:
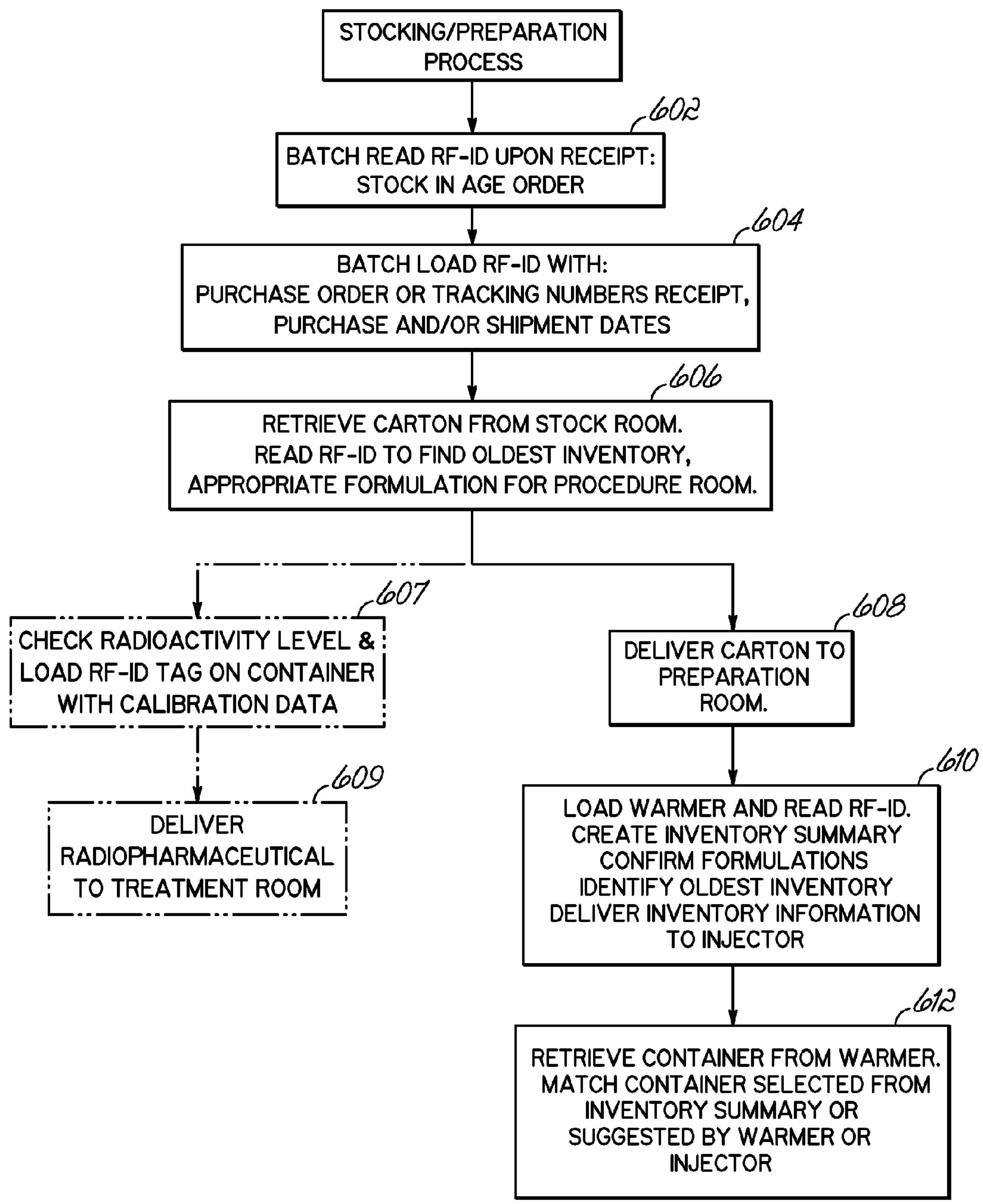
FIG. 7 is a flowchart of an exemplary method of stocking and preparing for use of a syringe or other container as shown in FIGS. 1A and 1B.

The cartons 34 then enter the distribution channel 40 and are received by a receiving department 44 of an imaging facility such as the hospital 42. An example of a syringe stocking and preparation process is illustrated in FIG. 7. Upon receiving the cartons 34, a R/W device 72 connected to a shipping/receiving computer 74 reads, at 602, the syringe RFID tags 60 and/or the shipping carton RFID tags 66. As shown in FIG. 3A, the shipping/receiving computer 74 stores the read data in an inventory database 76. The shipping/receiving computer 74 is connected via a communications link, for example, an Ethernet LAN, etc., to a hospital administration computer 78 and other computers; and one or more versions of the inventory database 76 can be maintained in any of those computers. Thus, the receiving computer 76, or another computer, is able to confirm that the delivered syringes conform to hospital purchase orders and, if applicable, automatically authorize payment of invoices therefor. Further, via the shipping/receiving computer 74, the syringe RFID tags 60 within the cartons 34 can, at 604, be updated with other data including, but not limited to:

- A time and date that the container was received.
- A hospital SKU code.
- Doctor related information.
- Patient related information.
- An identity of a stock room or other storage area.
- An identity of a particular preparation room and/or imaging suite in which the pharmaceutical is to be used.
- An identity of a particular power injector, which is to be used.

Thereafter, at 606, cartons are delivered to a room 46. As seen in FIGS. 3A and 1A, within the room 46, a R/W device 77 connected to a computer 79 can be used to read the syringe RFID tags 60 and update a database within the computer 79. Further, or alternatively, as shown in FIG. 3A, the computer 79, via the communications link 80, can be used to update the inventory database 76 within administration computer 78, thereby confirming delivery of the syringes to the room 46 from the shipping/receiving area 44.

The communications link 80 may be implemented by an Ethernet, USB, RS-232, RS-422, or other interface that uses a standard PC-based communications protocol, for example, BLUETOOTH, parallel, IrDA, ZigBee, 802.11b/g, or other comparable wired or wireless connection.

Subsequently, instructions are provided to move a shipping carton 34 from the room 46 to a preparation room 48. The R/W device 77 is used to read the RFID tags, at 606, and find the cartons 34 containing the desired syringes. Further, reading the RFID tags permits an identification of the oldest inventory. (Since contrast media has a shelf life, it may be appropriate to follow a first-in/first-out inventory procedure.) Thereafter, at 608, an identified shipping carton 34 is delivered to the preparation room 48.

Figure 4:
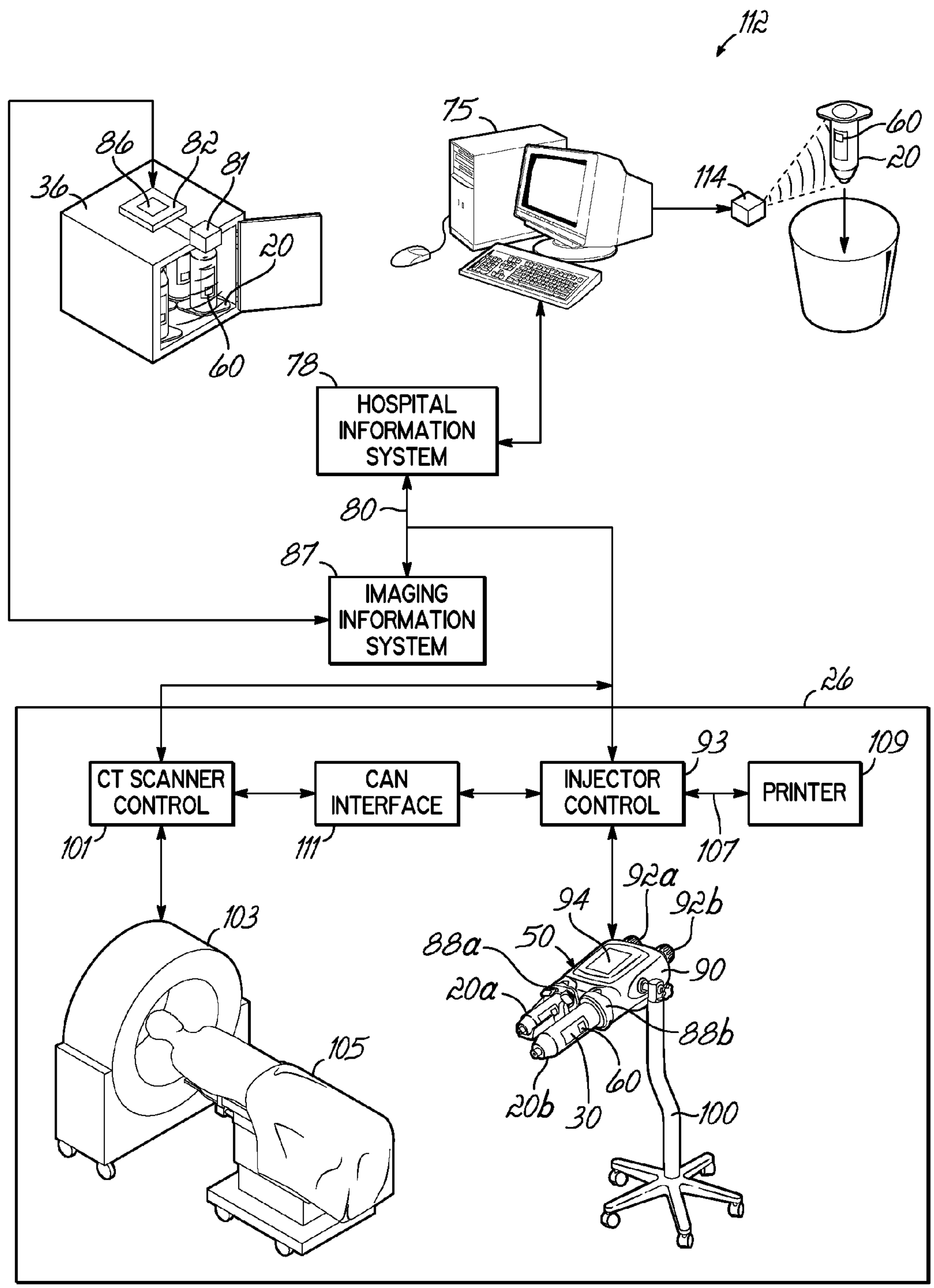
FIG. 4 is a schematic drawing illustrating activities and operations associated with use and disposal of a container of contrast media in an imaging suite.

In the preparation room 48, the syringes 20 are removed from a carton 34 and placed in the warmer 36 to bring the contrast media up to about body temperature. As shown in FIGS. 1A, 3A and 4, an R/W device 81 is connected to a warmer control 82 having a user interface 86. The warmer control 82 is electrically connected to an imaging information system 87 that, in turn, is connected to the communications link 80, and hence, to the other computers in the hospital 42. Upon placing a syringe in the warmer 36, the R/W device 81 reads, at 610, a respective RFID tag 60 and transmits data with respect to the syringe 20 to a work-in-process database 84 in the imaging information system 87 as illustrated n FIG. 3A.

Further, or alternatively, the imaging information system 87, via the communications link 80, can be used to update the inventory database 76, thereby allowing other computers to track information written to and read from the syringe RFID tags 60 in the warmer 36. R/W device 81 may also write to each RFID tag 60 the time and date each respective syringe 20 is placed in the warmer 36. Further, upon a technologist requesting, via the user interface 86, a particular contrast media, the warmer control 82 can, via the user interface 86, identify to the technologist a particular syringe inside the warmer 36, such as the syringe that has been in the warmer for the longest period of time. (Not only does contrast media have a limited shelf life, but the time spent in the warmer 36 should also be limited. Thus, inventory in the warmer 36 may also be handled on a first-in/first-out basis.) Upon removing a syringe 20 from the warmer, at 612, the R/W device 81 writes the removal time and date to a respective RFID tag 60 and reads data identifying the syringe being removed. The work-in-process database 84 and other databases are appropriately updated; and the warmer control 82 via the user interface 86 confirms to the technologist that the correct syringe has been removed.

Referring to FIGS. 1A, 3A, 4 and 5A, one or more syringes 20*a*, 20*b* are then carried into an imaging suite 26*a* and loaded into respectively one or both of the mounts or faceplates 88*a*, 88*b* that are attachable on a powerhead 90 of a powered fluid injector 50 in a known manner. In some embodiments, as latches 91 of the faceplates 88*a*, 88*b* are closed, the R/W device 104*a*, 104*b* is initiated to identify a specific RFID tag 60*a*, 60*b* and automatically read data from the specific tag 60*a*, 60*b*. An exemplary injector is shown and described in U.S. patent application Ser. No. 10/964,003, the entirety of which is hereby incorporated by reference. Although the powerhead 90 discussed herein is a dual head injector, embodiments of the present invention explicitly contemplate single head injectors as well. A suitable single-head injector is shown in U.S. Pat. No. 5,300,031, the entirety of which is hereby incorporated by reference.

In the illustrated application, in which the injector receives multiple syringes, a user-filled syringe having a volume of about 200 ml is mountable in a pressure jacket 250 of faceplate 88*a*. Further, a pre-filled syringe having a volume in excess of about 90 ml or more may also be mountable in faceplate 88*b*. The injector powerhead 90 includes hand-operated knobs 92*a* and 92*b* that are operative via an injector control circuit to control motors within respective plunger drives 95*a*, 95*b*. The plunger drives 95*a*, 95*b* are operable to move plungers within the respective syringes 20*a*, 20*b* in a known manner. Exemplary operations of a powerhead 90 and injector control 93 are shown and described in U.S. patent application Ser. No. 10/964,002, the entirety of which is hereby incorporated herein by reference. Additional exemplary operations are described in U.S. Pat. Nos. 5,662,612, 5,681,286 and 6,780,170, the entirety of which are hereby incorporated by reference. As seen in FIG. 3A, the injector control 93 is electrically connected to the hospital information system 78 via the communications link 80, and/or may be otherwise electrically connected to the imaging information system 87 by a communications link that uses a technology such as those noted above with reference to the communications link 80.

The injector powerhead 90 has a user interface 94, for example, a touch screen, for displaying current status and operating parameters of the injector 50. Powerhead 90 is often mounted to a wheeled stand 100, which permits easy positioning of the powerhead 90 in the vicinity of the examination subject 52. The injector 50 also has a remotely located console 96 with remote user interface 97, for example, a touch screen, a power supply 98 and other switches and components (not shown). The console 96 may be used by an operator to enter programs and control the operation of the injector 50 from a remote location in a known manner. In an embodiment, the touch screen of the user interface 94 or the console 96 may include a "start button" on the screen, which may be used to initiate the injection. Data is written to the RFID tag 60*a*, 60*b* when the start button is pressed by an operator, thereby initiating the dispensing of the medical fluid in the syringe 20*a*, 20*b* substantially simultaneously with the writing of the data to the RFID tag 60*a*, 60*b*. This data may include a status that the syringe 20*a*, 20*b* has been used. It will be appreciated that elements of the injector control 93 may be incorporated into the powerhead 90 or may be incorporated in other elements of the injector such as the power supply 98 or console 96, or may be distributed among these elements.

The faceplate 88*b* has an outward extending cradle 99 that supports a heater 106 mounted on a printed circuit ("PC") board 102. The heater 106 is electrically connected to the injector control via a cable or connector and is operable by the injector control 93 to heat the syringe 20*b* in a known manner. The PC board 102 further supports a R/W device 104*b* and an associated antenna system 229*b*. The R/W device 104*b* is also electrically connected to the injector control 93 and console 96. Further, the R/W device 104*b* may be activated by the injector control 93 to read data from an RFID tag 60*b* on a respective syringe 20*b*. Data may be written to, and/or read from, the RFID tag 60*b* at any specified time when a syringe 20*b* is in proximity of a respective faceplate 88, for example when the syringes 20*a*, 20*b* are loaded and the latches 91 of the faceplates 88*a*, 88*b* of the power injector are closed or when the powerhead 90 sends signals to the plunger drives 95*a*, 95*b* to initiate movement of the plunger(s), beginning the injection process. Thus, the system has the ability to determine when syringes 20*a*, 20*b* are mounted in the respective faceplates 88*a*, 88*b*. The data may be encrypted, and the data and data transfer may comply with 21 CFR 11, JCAHO, and HIPAA requirements.

Figure 8:
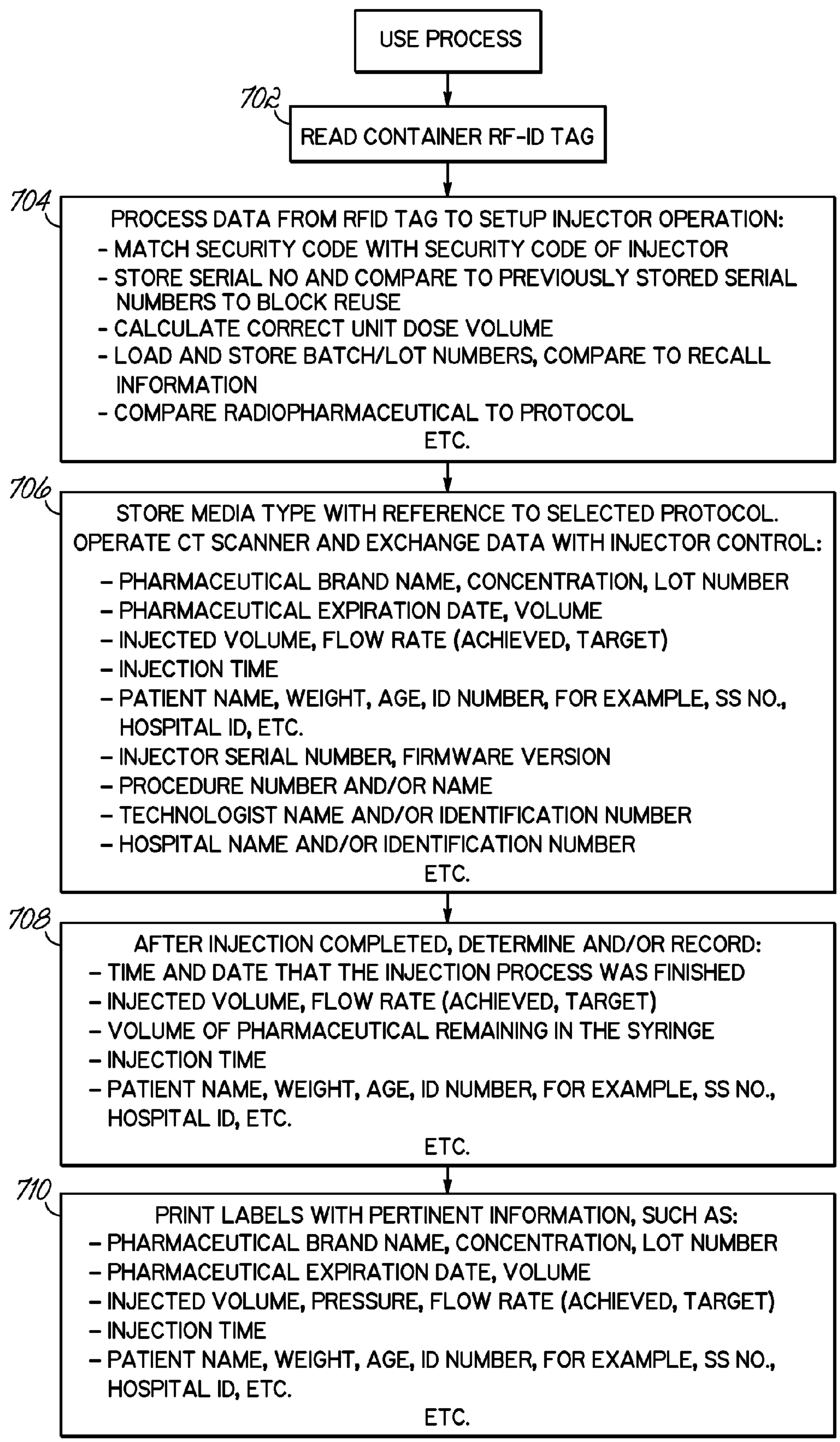
FIG. 8 is a flowchart of an exemplary method of using a syringe or other container as shown in FIGS. 1A and 1B.

One example of a process for utilizing the syringe 20*b* within the imaging suite 26*a* is shown in FIG. 8. This example is described principally with respect to the syringe 20*b* loaded in faceplate 88*b*; however the description is equally applicable to the syringe 20*a* loaded in faceplate 88*a*. The description is further applicable to an injection process in which media is dispensed from both syringes 20*a*, 20*b*, either sequentially or simultaneously. Simultaneous dispensing from both syringes may be done at controlled and selected flow rates to achieve any desired concentration of the resulting mixture of media and/or media and saline in the two syringes.

Referring to the process of FIG. 8, first, at 702, the R/W device 104*b* is activated to read data stored in the RFID tag 60*b* relating to contrast media or other pharmaceutical and its associated prefilled syringe or other container 20*b*. As shown at 704, that information includes, but is not limited to:

- A container identification and/or serial number that is checked against a database of previously used containers to block, if appropriate, a potential reuse of the container.
- A container security code, which may be matched with the security code of the injector being used.
- Information relating to container volume and volume delivery to assist the technologist in setting up the injector.

- Container volume and/or dimension information in order to provide a more precise real time dispensing control of volume.
- Pharmaceutical type and concentration data to confirm it is correct for a selected protocol.
- ID, batch and lot numbers that can be used to test the container and/or pharmaceutical against recall data.
- Shelf life data and fill date, which is compared to a current date to determine whether a recommended shelf life has been exceeded.

The R/W device 104*b* also writes the current time and date to the RFID device 60*b* to permit tracking of open-to-atmosphere time for the syringe 20*b*, which is also limited. During the contrast media injection process, the displacement of the syringe plunger is precisely controlled in accordance with data read from the RFID tag 60*b* relating to available syringe volume and/or dimensions thereof. Further, plunger feed is tracked, so that the contrast media remaining in the syringe can be continuously determined.

The faceplates 88*a*, 88*b* have a bidirectional communications link with the injector control 93, which may be used to transfer any of the above information between the syringes 20*a*, 20*b* and the injector control 93. Thus, the injector control 93 may have syringe and drug information that may facilitate a procedure setup and result in reduced time and error. In addition, the injector control 93 may read or write other information to and from the faceplates 88*a*, 88*b*, which is not directly pertinent to syringe information. Examples of this may include, but are not limited to:

- Enabling or disabling of the faceplate electronics.
- Heating of the faceplate for contrast media warming.

In step 706 of FIG. 8, the media is used in connection with a procedure. As seen in FIG. 4, before, during and after injection of the contrast media, a technologist operates a CT scanner control 101 that is effective to cause a CT scanner 103 to scan a patient 105 shown in phantom. The injector control 93 may have one or more interfaces to a CAN communications bus 111, which is a known interface for the CT scanner control 101. The protocol is defined by the scanner manufacturers. Data and data transfer between the injector and scanner comply with 21 CFR 11, JCAHO, and HIPAA requirements.

Returning to FIG. 8, as shown at 706, data transfer between the injector control 93 and CT scanner control 101 may be bi-directional and may relate to the contrast media or other pharmaceutical and its associated prefilled syringe or other container 20*b*. Such data includes, but is not limited to, the following:

- Pharmaceutical brand name, concentration, lot number.
- Pharmaceutical expiration date, volume.
- Injected volume, flow rate (achieved, target).
- Injection time.
- Patient name, weight, age, ID number, for example, SS no., hospital ID, etc.
- Injector serial number, firmware version.
- Procedure number and/or name.
- Technologist name and/or identification number.
- Hospital name and/or identification number.
- Used or unused status of container.
- CT scanner setup and procedure information.
- CT scanner ID and/or serial no.
- CT images.
- Hospital information system data.
- Injector functional control.
- CT scanner functional control.

Upon the injector control 93 determining that the desired volume of contrast media has been delivered, the injection process is stopped. At the end of the injection process, as shown in FIG. 8 at 708, the injector control 93 is operative to determine an exact volume of contrast media injected; and the injector control writes to the RFID tag 60*b* and/or updates the imaging information system 87 with data and information that includes, but is not limited to the following:

- Time and date that the injection process was finished.
- Injected volume, flow rate (achieved, target).
- Volume of pharmaceutical remaining in the container.
- Injection time.
- Patient name, weight, age, ID number, for example, SS no., hospital ID, etc.
- Injector serial number, firmware version.
- Procedure number and/or name.
- Technologist name and/or identification number.
- Hospital name and/or identification number.
- Used or unused status of syringe.
- CT Scanner Information.

As illustrated in FIG. 4, the injector control 93 has an interface providing a communications link 107 to a hard-copy printer 109. The printer 109 may be, but is not limited to, a thermal, ink-jet, or laser based printer. The printer 109 may be used to print pages and/or labels of various sizes and colors at specified times upon requests of a user, the CT scanner control 101, the hospital information system 78, or the injector control 93. The labels may be made part of patient records, requisition sheets, or other forms. Data output and data transfer may comply with 21 CFR 11, JCAHO, and HIPAA requirements/

Returning to FIG. 8, as shown at 710, a label or page may be printed to provide information relating to the contrast media or other pharmaceutical, its associated prefilled syringe or other container 20*b*, and the use thereof. Such information includes, but is not limited to, the following:

- Pharmaceutical brand name, concentration, lot number.
- Pharmaceutical expiration date, volume.
- Injected volume, pressure, flow rate (achieved, target).
- Injection time.
- Patient name, weight, age, ID number, for example, SS no., hospital ID, etc.
- Injector serial number, firmware version.
- Procedure number and/or name.
- Technologist name and/or identification number.
- Hospital name and/or identification number.
- Used or unused status of syringe.
- Graphs or charts, for example, pressure, flow rate, etc.
- CT scanner information.
- CT scan information.
- Open (white) space or blanks for tech initials, drawings, etc.

Thus, any of the above information can be exchanged between the injector control 93 and hospital information system 78. Potential uses for this capability include but are not limited to:

- Electronic inclusion of volume of contrast media injected and other procedure information in patient record.
- Electronic re-ordering of supplies.
- Automated billing.
- Automated scheduling.

At the initiation of or after the injection process, the injector control 93 can write to the RFID tag 60*b* to set a syringe-used flag that will help to prevent a reuse of the syringe 20*b*. The syringe 20*b* is then removed from the faceplate 88*b*; and if the procedure was aborted and the syringe was not used, it can be placed back into the warmer 36. In that process, information is read from, and written to, the RFID tag 60*b* as previously described. Further, the image information system 87 is also able to track the open-to-atmosphere time of the syringe and warn the technologists when an open-to-atmosphere time is exceeded.

If the syringe 20*b* removed from the faceplate 88*b* is empty, the syringe is typically transported to a disposal area 112 (FIGS. 1A, 3A and 4); and prior to disposal, another R/W device 114 connected to one of the other computers 75 reads the RFID tag 60*b*. The inventory database 76 can thus track the identity of the syringe 20 being destroyed. Further, the syringe disposal information can be communicated to a supplier computer 116 via a communications link 118 as seen in FIG. 3A, for example, via the Internet 83, a telephonic connection, or other comparable wired or wireless connection.

In an alternative embodiment, empty syringes, instead of being destroyed, are returned to the supplier 24 for further processing, for example, disposal or refilling. In the latter example, the syringes 20 pass through the hospital shipping/receiving area 44 and the RFID tags are again read to identify the syringes leaving the hospital; and the inventory database 76 is updated accordingly. Upon entering the supplier shipping/receiving area 38, the RFID tags 60*b* are again read to update a supplier inventory database 120 tracking syringes within the supplier's facilities. The RFID tags 60*b* on the syringes 20 are updated or replaced depending on whether the syringe is destroyed or reconditioned and refilled by the supplier.

In the system shown and described herein, the injector control 93 facilitates information collection and transfer throughout a CT procedure. The RFID-enabled syringes provide quicker and more accurate data recording, as well as an automated transfer of drug information. The printer allows for a hard copy of selected information to be incorporated into the patient or hospital record. The CT interface via CAN, facilitates information flow and collection at a single point, either the CT scanner system or the injector. The hospital information system interface improves this information flow a step further, potentially creating an all-electronic system with minimal user intervention; this provides the opportunity for reduced error and efficiency in the CT scanning suite.

Figure 5B:
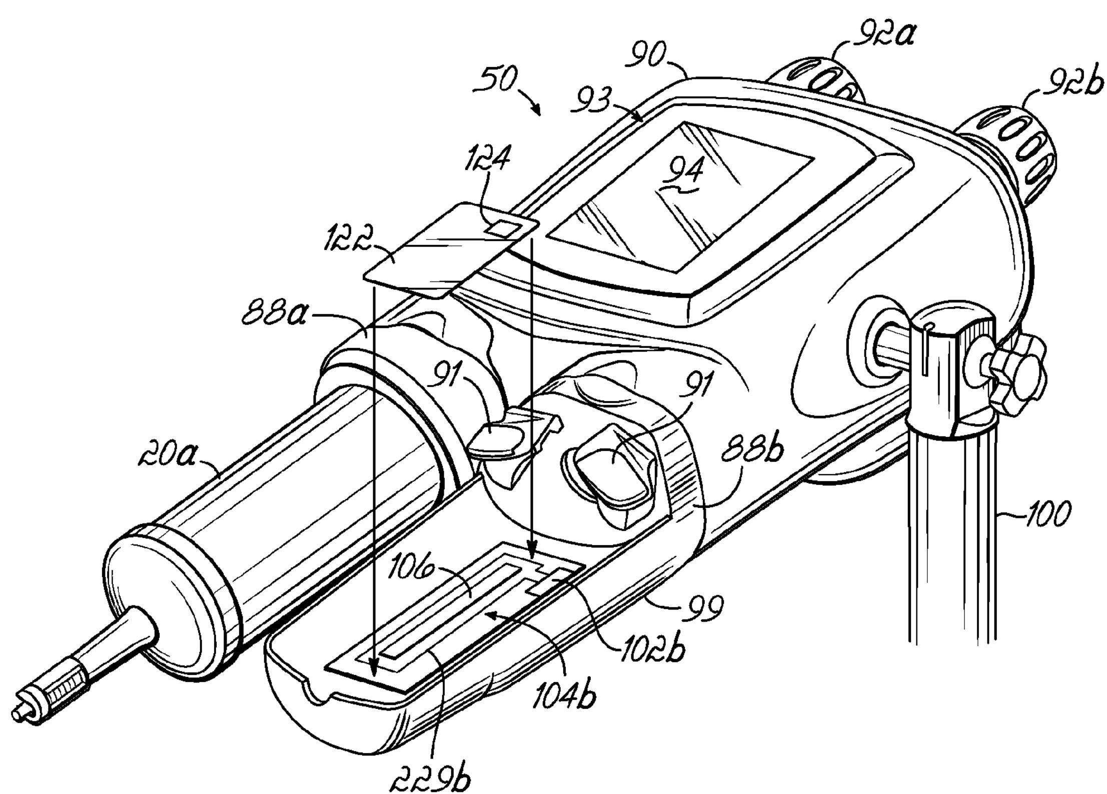
FIG. 5B is a perspective view of an embodiment of an injector and a field engineer identification card that may be used in the system of FIG. 1A.

With respect to another exemplary embodiment, on occasion, field engineers make service calls to a power injector, e.g. for routine maintenance or to diagnose failed operation. During such service calls, the field engineer is able to operate the injector in a "service" mode without having to install electrical jumpers in the injector control. Instead, referring to FIG. 5B, the service mode function is initiated by a field engineer using an intelligent identification ("ID") card 122. Such an ID card 122 has an RFID tag 124 that incorporates an RFID chip and associated antenna in a known manner.

Figure 9:
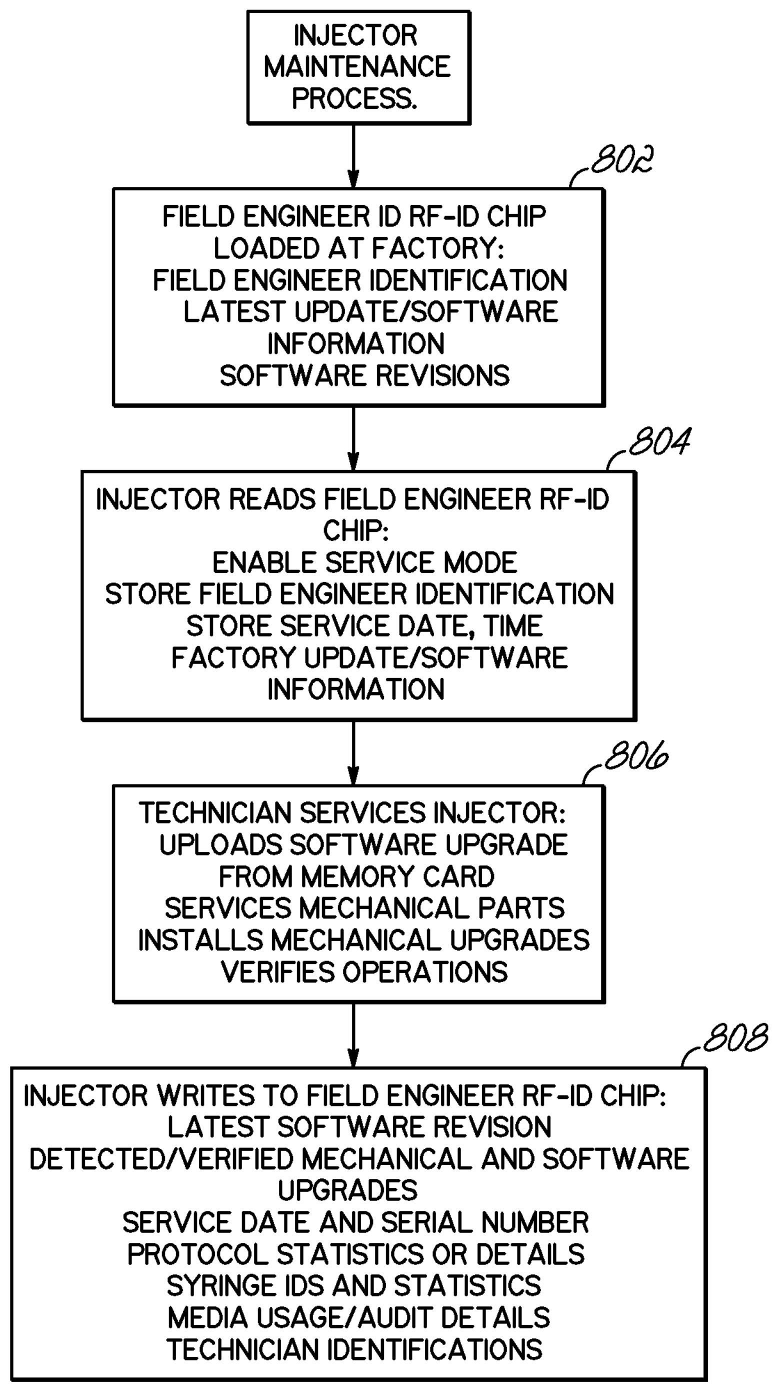
FIG. 9 is a flowchart of an exemplary method of a field maintenance process for a syringe filled with contrast media as shown in FIG. 1A.

An exemplary process for using the ID card 122 for injector maintenance is shown in FIG. 9. As indicated at 802, the RFID tag 124 is loaded at the supplier facility 24 with data including, but not limited to, the following:

An identification of the field engineer.

Latest updates and software information.

Specific software revisions.

To initiate service of a power injector, the field engineer places the ID card 122 on an empty faceplate 88*b*, thereby allowing the R/W device 104*b* to read and write to the RFID tag 124. As indicated at 804 of FIG. 9, upon reading an appropriate identification and security code from the RFID tag 124, a field engineer identification and service time and date are stored in the injector control 93. Thereafter, the injector user interfaces 94, 97 (see FIG. 5A) are effective to switch the injector 50 into a service mode, thereby disabling several operational checks and features that are used in a normal injection cycle but which inhibit operating the injector 50 for service purposes. The R/W device 104 continues to periodically read the identification and security codes from the RFID tag 124. Upon failure to successfully read the RFID tag 124, for example, because the ID card 122 has been removed from the faceplate 88*b*, the injector control 93 automatically switches the injector 50 out of the service mode. Thus, the previously disabled operational checks and features are re-enabled, and the injector is ready to operate in a normal injection cycle. Further, at 804, the injector control 93 is operative to read from the RFID tag 124 information and data relating to factory updates to the injector components and software.

In the process of servicing the injector 50, as indicated at 806, the field engineer initiates uploads of software upgrades from the RFID tag 124 to the injector control 93. In addition, mechanical components are serviced, mechanical upgrades are installed and their operation is verified. As a final step of the service operation as indicated at 808, the injector control 93 writes to the RFID tag 124 on the ID card 122 data including, but not limited to, the following:

The latest software revision installed.

A confirmation that mechanical and software upgrades have been installed.

The date of service and serial number of the injector.

Protocol, statistics or details relating to the injector operation since the last service.

Upon the field engineer returning to the supplier facility 24, the RFID tag 124 is read; and the service information is stored in a history file associated with the particular injector that was serviced.

The use of an RF communications system between an RFID tag 60 on a container 20 and a power injector control 93 provides for further exemplary embodiments of the RF communications system. Known RFID systems use electromagnetic (EM) fields to communicate between an R/W device that includes a tuned antenna and one or more RFID tags or transponders. In one exemplary embodiment, the R/W device sends out data using EM fields at a specific frequency; and with passive RFID tags, this EM energy powers the tag, which in turn enables processing of this received data. Following receipt of the data, the RFID tag may transmit data that is received and processed by the R/W device.

Figure 10:
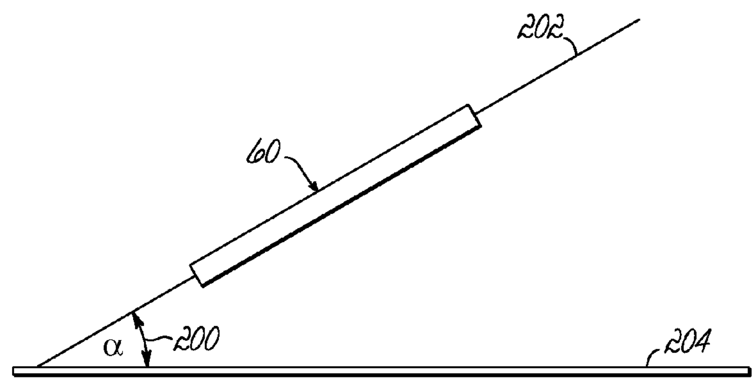
FIG. 10 is a schematic drawing illustrating a variation in RF signal strength in coupling a transmitting antenna with a receiving antenna angled with respect to the transmitting antenna.

An RFID is difficult to implement around metallic or diamagnetic materials, for example, water, saline or a medical fluid in a container such as a contrast media in a syringe. These materials absorb and/or reflect RF energy, making successful read-write RFID operations difficult, especially with the low power regulations for RF frequencies. In addition, the angle between a plane of the RFID tag antenna and a plane of the R/W device antenna is critical. For optimum performance, the plane of the RFID tag antenna should be substantially parallel to the plane of the R/W device antenna. As shown in FIG. 10, for single plane antennas, as an acute angle 200 between an RFID tag antenna plane 202 and an R/W device antenna plane 204 increases, a signal strength coupling the antennas in the two planes 200, 204 decreases. In other words, as the angle 200 increases, the RF signal strength transferable from the R/W device antenna to the RFID tag antenna decreases. Similarly, the signal strength transferable from the RFID tag antenna back to the R/W device antenna also diminishes. Further, that signal strength is substantially equal to the output signal strength of the R/W device antenna minus any attenuation from metallic and diamagnetic materials divided by the cosine of the angle 200.

Figure 11:
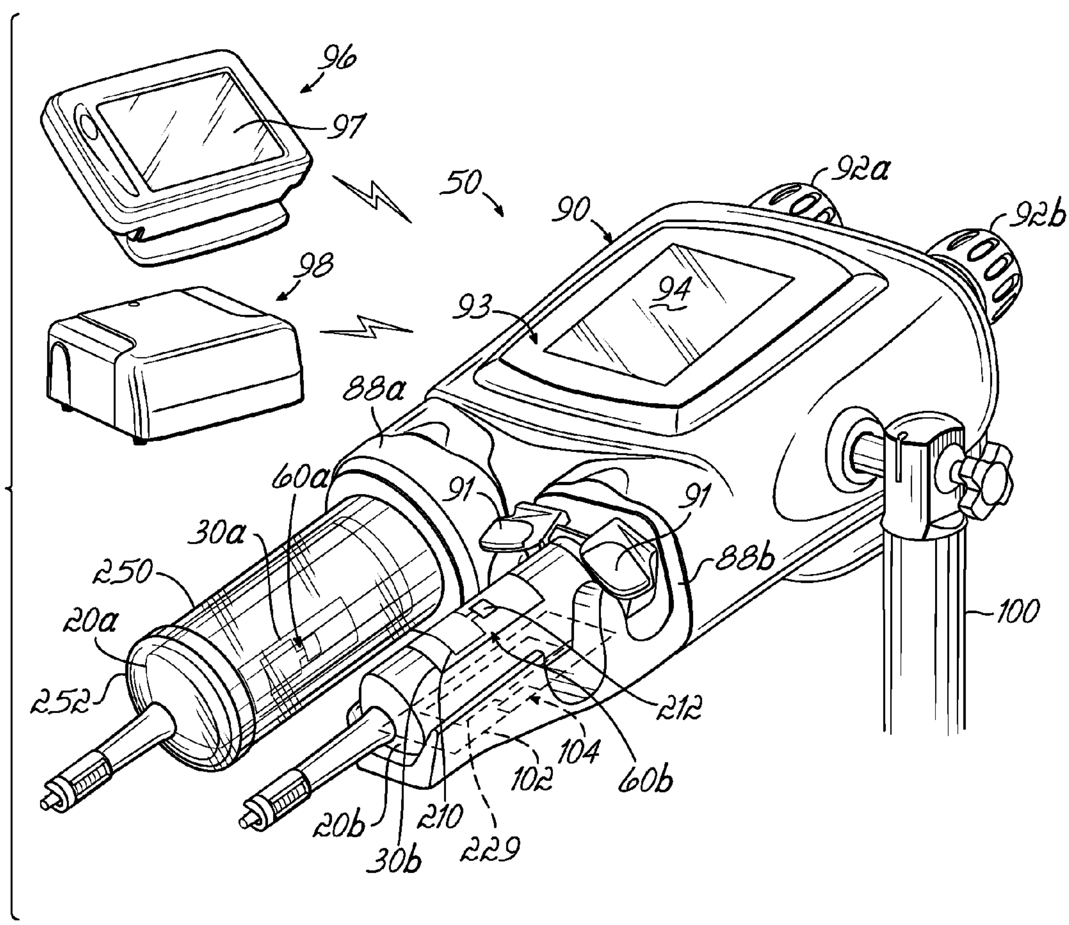
FIG. 11 is perspective view of a contrast media power injector having an RF data tag on a syringe mounted in a power injector.

Referring back to FIG. 5A, orientation of the syringe 20*b* places the RFID tag antenna 210 relatively close to the R/W device 104*b*; and therefore, coupling RF signals therebetween to facilitate reading data from, and/or writing data to, the RFID tag 60*b*. However, with the syringe 20*b* oriented as shown in FIG. 11, contrast media in the syringe 20*b* is between the RFID tag antenna 210 and the R/W device 104*b*. The contrast media attenuates the RF field strength from the antenna of the R/W device 104*b* and interferes with its RF coupling with the RFID tag antenna 210.

Figure 12:
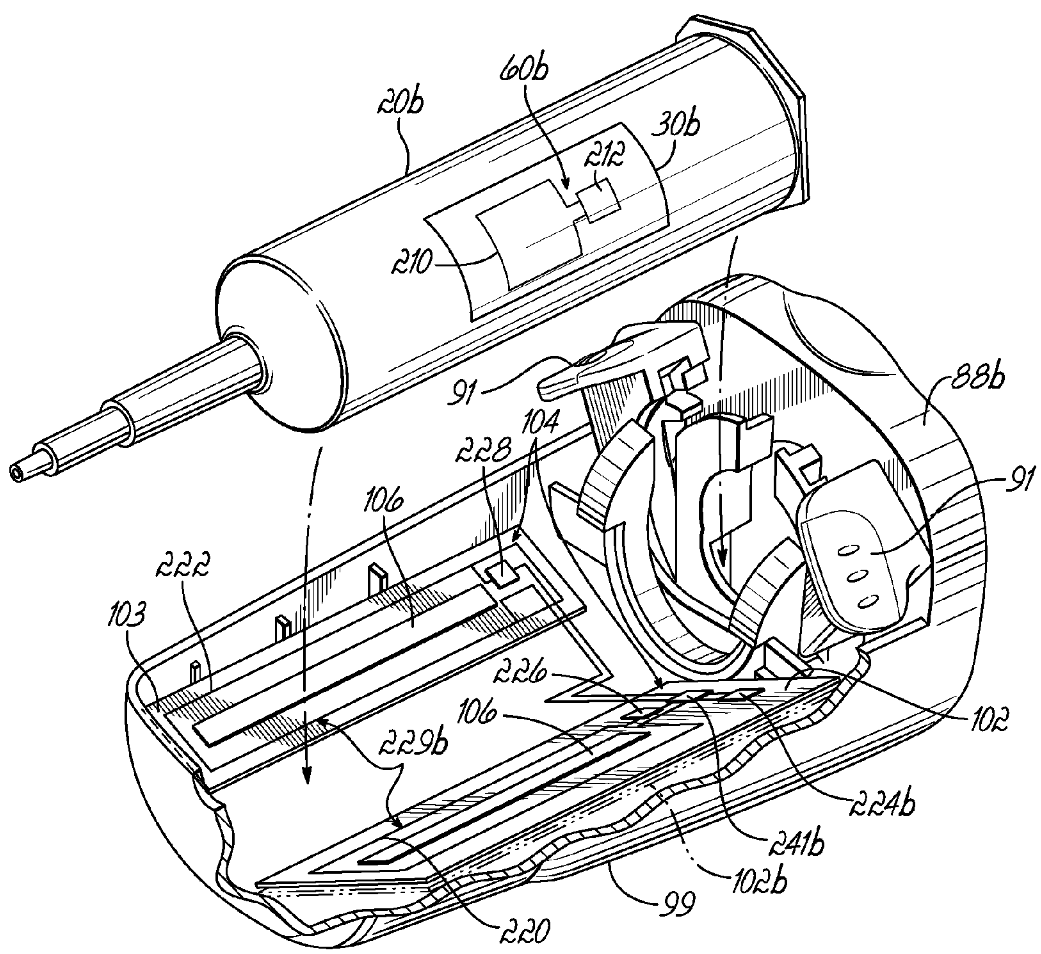
FIG. 12 is a perspective view of an exemplary embodiment illustrating a syringe positioned above a faceplate of a contrast media power injector having multiple, nonparallel antenna loops for a read/write device in accordance with the principles of the present invention.

In one exemplary embodiment of the invention, referring to FIG. 12, a syringe 20*b* having a label 30*b* with an antenna 210 and RF driver 212 is positioned above faceplate 88*b*, ready to be loaded therein. A first PC board 102 and a second PC board 103 are mounted in faceplate 88*b*, so as to be nonparallel. The PC boards 102, 103 form sides of a V-shape and thus, form an angle of less than 180 degrees therebetween. PC board 102 supports a first antenna loop 220 and its associated tuning circuit 226, and PC board 103 supports a second antenna loop 222 and its associated tuning circuit 228. The first and second antenna loops 220, 222 and respective tuning circuits 226, 228 are connected to an R/W RF driver circuit 224*b* through a switching circuit 241*b* to collectively form the electromagnetic R/W device 104*b*. In an alternative embodiment, the R/W RF driver circuit 224*b* and switching circuit 241*b* may be mounted on a separate PC board 102*b* (shown in phantom), which is located beneath, and electrically connected to, the PC board 102. In other embodiments, the R/W RF driver circuit 224*b* and/or the switching circuit 241*b* may be mounted in the power head 90 in association with the injector control 93.

Further, as shown in FIGS. 13A-13D, an antenna system 229*b* comprising the antenna loops 220, 222, respective tuning circuits 226, 228 and switching circuit 241*b* is connectable in different electrical configurations to achieve an optimum RF coupling between the R/W device 104*b* and the RFID tag 60*b*.

Figure 13A:
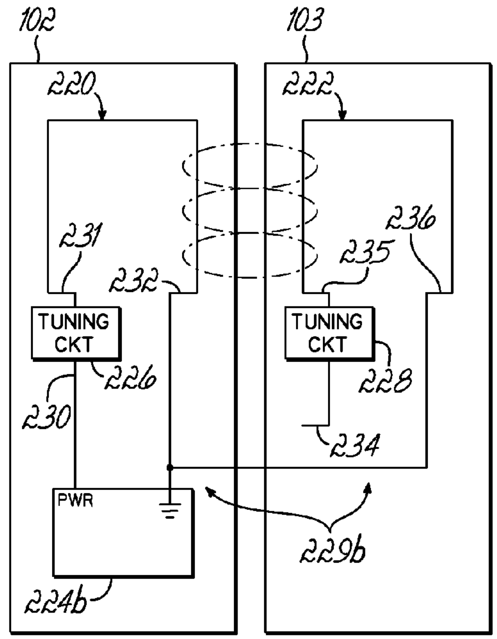
FIGS. 13A-13D are schematic drawings of four different circuit configurations for the multiple, nonparallel antenna loops of FIG. 12.

Referring to FIG. 13A, power from the R/W RF driver circuit 224*b* is applied to the input 230 of a tuning circuit 226 that is connected to a signal lead 231 of the primary antenna loop 220 on PC board 102. Further, input 234 of the tuning circuit 228, which is connected to a signal lead 235 of the secondary antenna loop 222 on PC board 103, is left open or floating. A primary antenna loop ground lead 232 is connected to ground with the secondary antenna loop ground lead 236. In this configuration, the powered primary antenna loop 220 on PC board 102 is tuned to a frequency indicated by a protocol of the RFID tag 60*b*, for example, about 13.56 Megahertz, which permits propagation of the RF signal into the surrounding area. An RF signal from the primary antenna loop 220 is coupled with the secondary antenna loop 222 on PC board 103, because the secondary antenna loop 222 is also tuned to resonate at about 13.56 Megahertz.

Figure 13B:
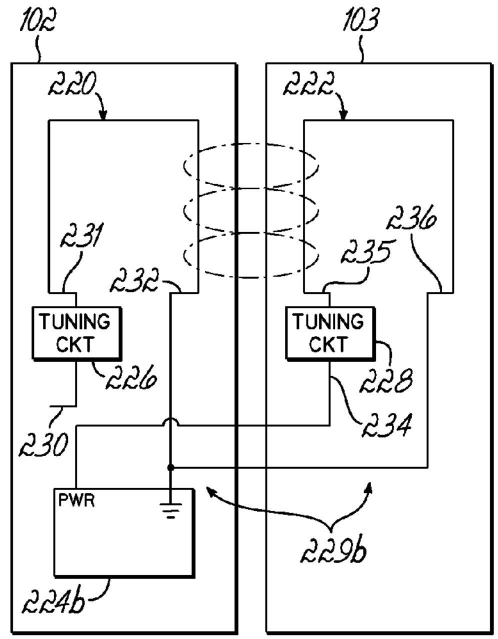

The angled, V-shape orientation of the PC boards 102, 103 and respective areas of antenna loops 220, 222 provide an expanded or increased total antenna area for the R/W device 104*b*. Thus, with the antenna configuration of FIG. 13A, as shown in FIG. 12, an effective antenna area extends circumferentially around a substantially greater area of a syringe 20*b* than is possible with the single PC board 102 shown in FIG. 5A. Further, the antenna power provided by the RF driver circuit 224*b* is also spread over a larger area represented by the combined areas of antenna loops 220, 222. Upon the syringe 20*b* being loaded onto the faceplate 88*b*, with some orientations of the syringe 20*b*, the larger antenna area shown in FIG. 13A improves the RF coupling with the antenna 210 of the RFID tag 60*b*. As shown in FIG. 13B, antenna loop 222 on PC board 103 can be made the primary loop by disconnecting or opening an input 230 of the tuning circuit 226 and connecting the tuning circuit input 234 of the antenna loop 222 to the power output of the R/W RF driver circuit 224*b*. First antenna loop ground lead 232 and second antenna loop ground lead 236 continue to be connected to ground. Again, both antenna loops 220, 222 are tuned to resonate at the RFID tag frequency, that is, about 13.56 Megahertz. The antenna configuration of FIG. 13B may provide better RF coupling with the antenna 210 of the RFID tag 60*b* depending on the orientation of the syringe 20*b* and thus, the circumferential location of the RFID tag 60*b*.

Figure 13C:
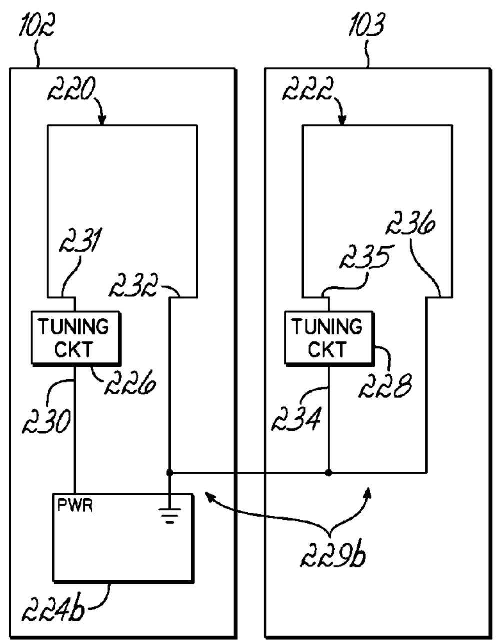

Another configuration of the antenna loops 220, 222 is shown in FIG. 13C wherein the tuning circuit input 230 of the first antenna loop 220 is connected to the power output of the R/W RF driver circuit 224*b*; and first antenna loop ground lead 232 is connected to ground. The tuning circuit input 234 and ground lead 236 of antenna loop 222 are connected to ground, which prevents the second antenna loop 222 from resonating at the RFID tag frequency, which, in this application, is 13.56 MHz. This effectively reduces the area of the antenna system 229*b* to the area of the primary antenna loop 220, and all of the power from the R/W RF driver circuit 224*b* is applied across the area of the primary antenna loop 220, which is tuned to resonate at the RFID tag frequency, that is, about 13.56 Megahertz. Upon the syringe 20*b* being loaded onto the faceplate 88*b*, depending on the orientation of the syringe 20*b* and the RFID tag antenna 210, the smaller antenna area of the circuit in FIG. 13C may improve the RF coupling with the antenna 210 of the RFID tag 60*b*.

Figure 13D:
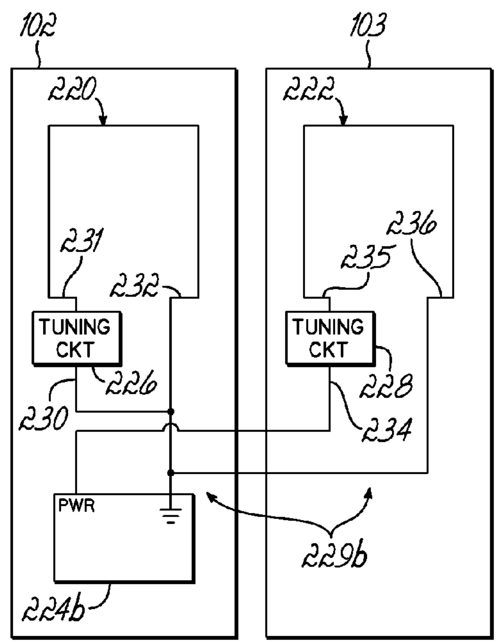

Referring to FIG. 13D, alternatively to FIG. 13C, the tuning circuit input 234 of the second antenna loop 222 on PC board 103 is connected to the power output of the R/W RF driver circuit 224*b*; and tuning circuit input 230 of the first antenna loop 220 is connected to ground along with antenna loop ground leads 232 and 236. Thus, the first antenna loop 220 does not resonate at the RFID tag frequency of 13.56 MHz; and only the second antenna loop 222 is tuned to resonate at that frequency. With some orientations of the syringe 20*b*, this antenna configuration provides the best RF coupling with the antenna 210 of the RFID tag 60*b*.

In some applications, a user may be instructed to load the syringe 20*b* in the faceplate 88*b* so that the label 30*b* is always in the same orientation. Or, in other applications, the RFID tag 60*b* may be removable from the syringe and mountable at a fixed location on the injector 50. In those applications, an R/W antenna can be designed and placed in a fixed location to have optimum RF coupling with an RFID tag. However, in still further applications, a user may have no limitations on where the RFID tag 60*b* is located on the syringe 20*b* or how the RFID tag 60*b* is oriented when the syringe 20*b* is mounted on a faceplate 88*b*. In those applications, the RFID tag 60*b* may have any circumferential location around a barrel of the syringe 20*b* or within the faceplate 88*b*. Further, in such applications, it is difficult to precisely predict which of the antenna configurations in FIGS. 13A-13D will provide the best RF coupling with an RFID tag having an unknown orientation with respect to R/W device 104*b*. This is due, in part, to the complex and somewhat unpredictable EM fields formed around materials that reflect and/or absorb such fields. Therefore, in another exemplary embodiment of the invention, all of the antenna configurations of FIGS. 13A-13B may be utilized.

Figure 14:
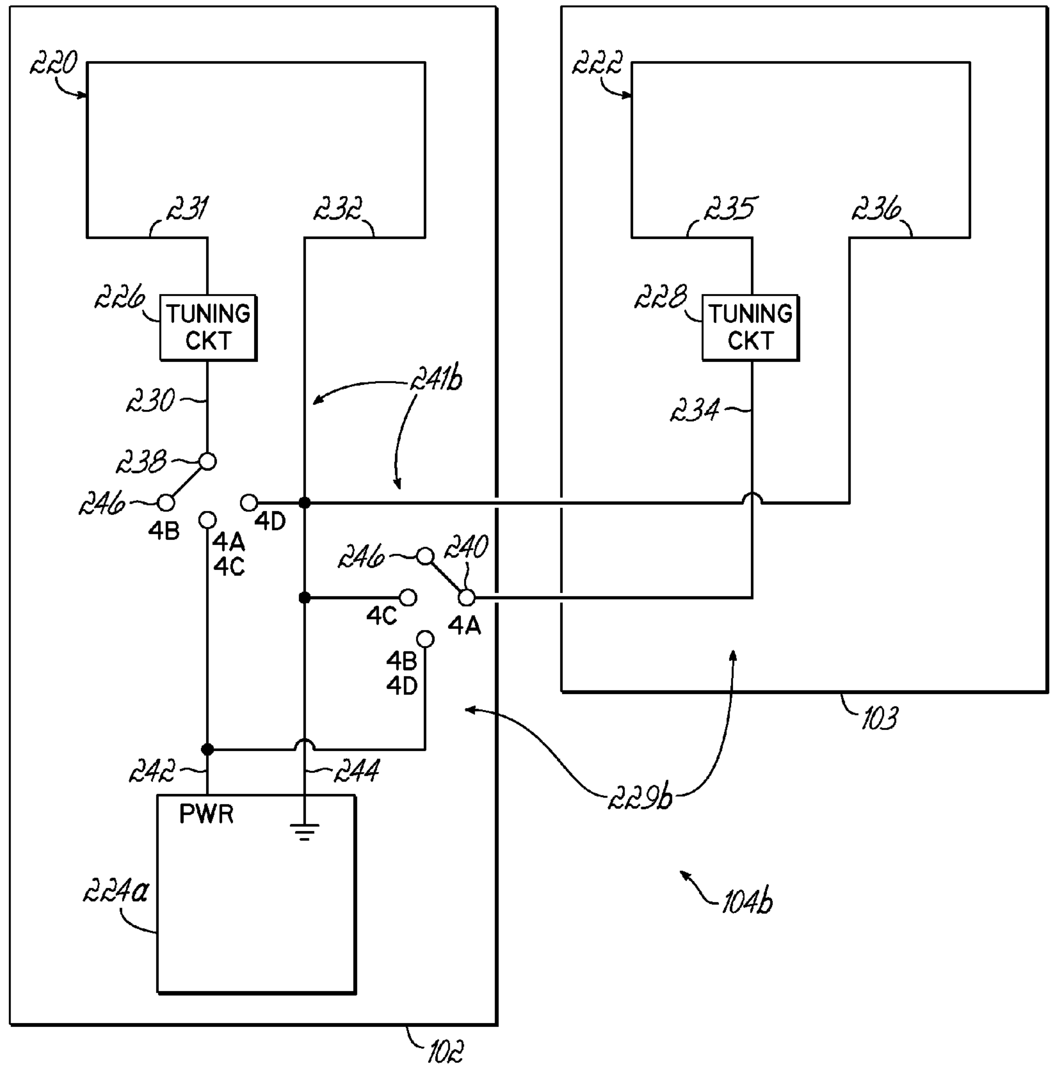
FIG. 14 is a schematic drawing of the multiple, nonparallel antenna loops of FIG. 11 with switches for connecting the antenna loops in the four different circuit configurations of FIGS. 13A-13D.

Referring to FIG. 14, switches 238, 240 on PC board 102 comprise the switching circuit 241*b*, which is used to selectively connect respective tuning circuit inputs 230, 234 to either a power output or terminal 242 from R/W RF driver circuit 224*b*, a ground terminal 244 or an open state represented by contacts 246. The ground leads 232, 236 of respective antenna loops 220, 222 are always connected to the ground 244. The contacts of switches 238, 240 have notations to FIGS. 13A-13D indicating the switch states corresponding to the antenna configurations of FIGS. 13A-13D.

Figure 15:
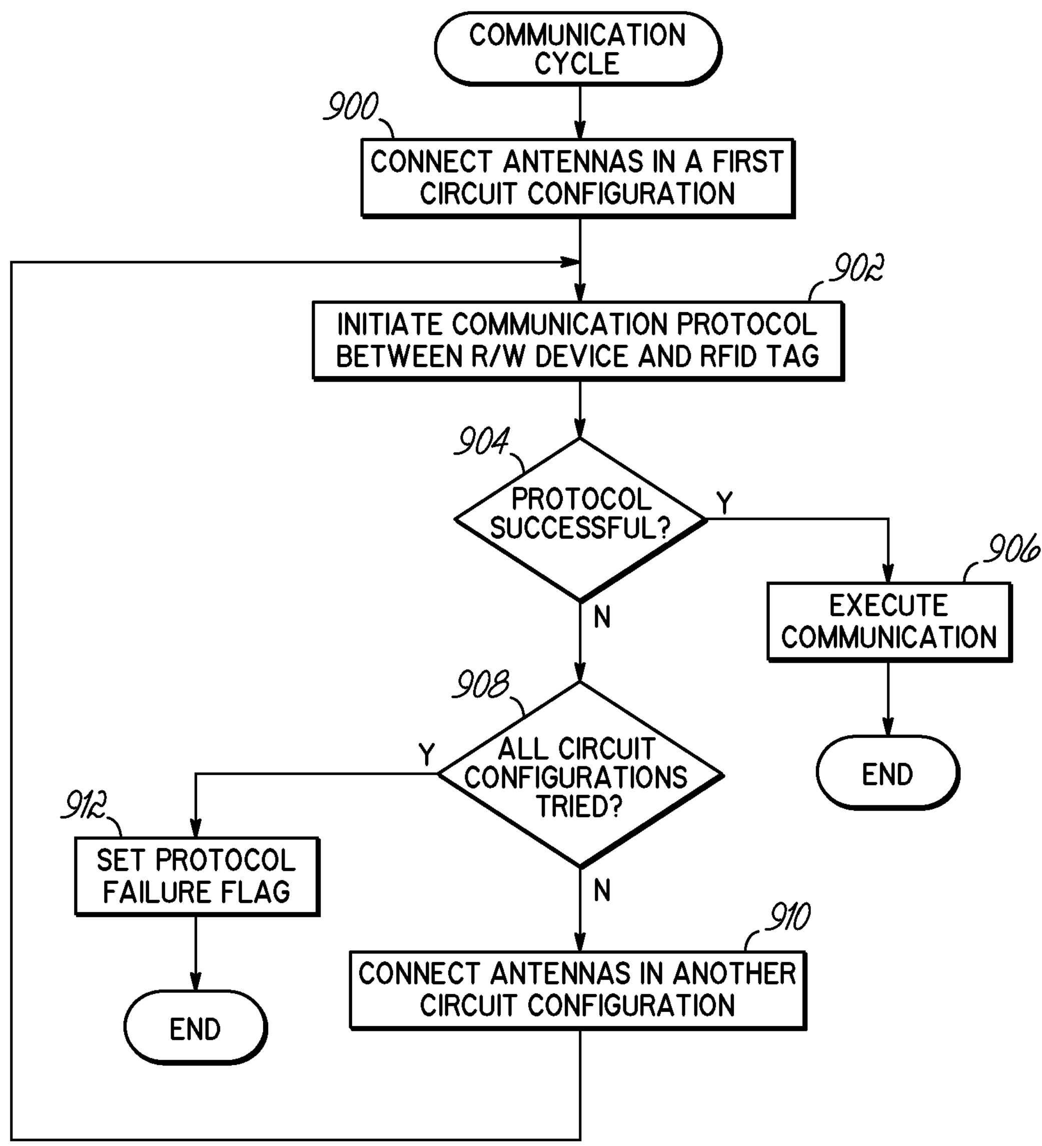
FIG. 15 is schematic drawing of a flowchart illustrating a communications cycle utilizing the multiple, nonparallel antenna loops of FIG. 12.

In use, referring to FIGS. 12 and 15, a communications cycle is initiated either automatically by the injector control 93 detecting a syringe 20*b* being loaded into the faceplate 88*b* (such as by the movement of a mounting arm of the faceplate 88*b*, causing a magnet in the mounting arm to move into confronting relationship with a magnetic sensor in the injector), or manually by an operator providing an input to the injector control 93. In either event, the injector control, at 900, operates the switches 238, 240 to connect the antenna loops 220, 222 in a first of the four circuit configurations, for example, the circuit configuration shown in FIG. 13A. Thereafter, the injector control 93 initiates, at 902, a communications protocol between the R/W RF driver circuit 224*b* and the RF driver circuit 212 of the RFID tag 60*b*. Initiating a communications protocol is a known process by which the R/W RF driver circuit 224*b* causes the R/W antenna system 229*b* to emit an electromagnetic signal in order to establish a reliable RF coupling with the tag antenna 210 and thus, establish an RF communications with the RFID tag 60*b*. Upon establishing an RF communications, the R/W device 104*b* can read data from and/or write data to the RFID tag 60*b*.

If, at 904, the injector control 93 determines that the communications protocol and hence, the RF communications link, has been established, the injector control 93 commands, at 906, the R/W drive 104*b* to proceed with the reading of data from, and/or the writing of data to, the RFID tag 60*b*. However, if, at 904, the injector control 93 determines that the communications protocol failed, and a successful RF communications between the R/W device 104*b* and the RFID tag 60*b* is not made, the injector control 93 determines, at 908, whether all antenna loop configurations have been tried. If not, the injector control 93 operates, at 910, the switches 238, 240 to connect the antenna loops 220, 222 into another one of the four circuit configurations shown in FIGS. 13A-13B. Thereafter, the injector control 93 automatically iterates through the process steps 902-908 to reconnect the antenna loops 220-222 in different circuit configurations in an attempt to establish a successful RF communications protocol or link. If, at 908, the injector control 93 has tried all of the antenna loop configurations without success, it sets, at 912, a protocol failure flag or error message.

FIGS. 11-14 illustrate different embodiments of an antenna system 229*b* that may be employed with an electromagnetic R/W device 104*b* to read a data tag 60*b* applied to a syringe 20*b* mounted in an open faceplate 88*b*. In a further embodiment, referring to FIG. 5A, a syringe 20*a*, that often is a user-filled disposable syringe, is mounted within a translucent or transparent pressure jacket 250 of faceplate 88*a*. The syringe 20*a* is secured in the pressure jacket 250 by a cap 252 in a known manner. A data tag 60*a* is integrated into a label 30*a* applied to the syringe 20*a*, and the structure and operation of data tag 60*a* is substantially identical to the data tag 60*b* previously described. When utilizing the pressure jacket 250 of faceplate 88*a*, it is desirable that the data tag 60*a* be readable regardless of its orientation inside the pressure jacket 250.

Figure 16:
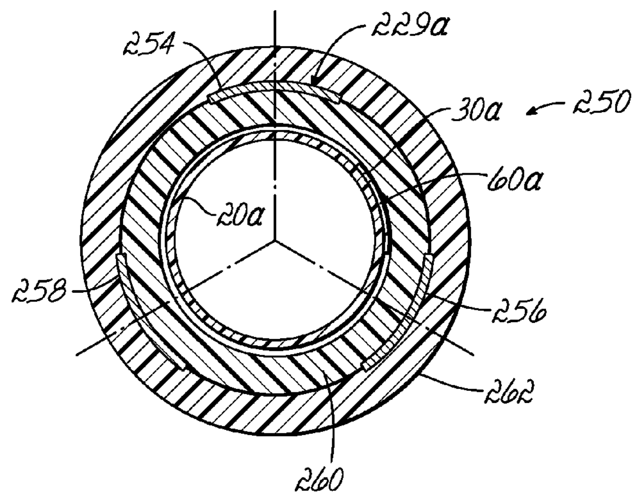
FIG. 16 is a cross-sectional drawing of a pressure jacket for a contrast media power injector as shown in FIG. 11, which is equipped with a multiple loop, nonparallel antenna system for the contrast media power injector similar to that illustrated in FIG. 12.
Figure 17:
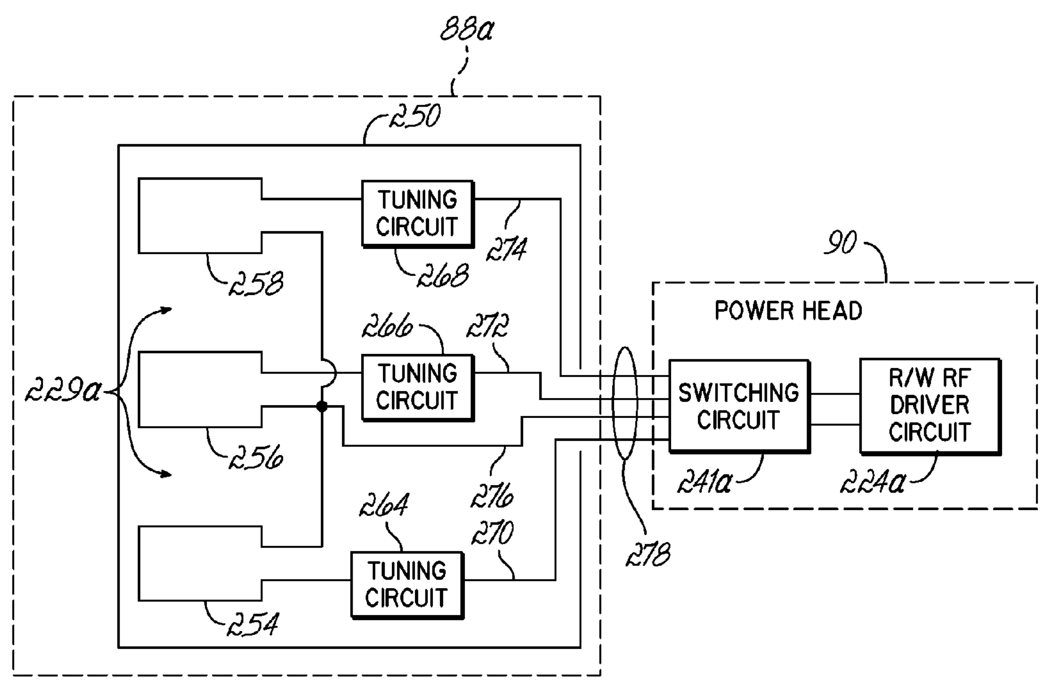
FIG. 17 is a schematic drawing of an electromagnetic radio frequency R/W device utilizing the multiple loop, nonparallel antenna system of FIG. 16.

Referring to FIGS. 5A and 16, in a further exemplary embodiment of an RFID communications system, to enhance readability of a data tag 60*a*, the pressure jacket 250 may be equipped with an antenna system 229*a*, which includes of an array of antenna loops 254, 256, 258 spaced about a circumference of the syringe 20*a*. While equal spacing of the antenna loops is shown, other spacing may be used. The pressure jacket 250 has inner and outer cylindrical sleeves 260, 262, respectively. As illustrated, the antenna loops 254, 256, 258 may be molded between the inner and outer sleeves 260, 262. Referring to FIG. 17, the antenna loops 254, 256, 258 have respective tuning circuits 264, 266, 268, which may be molded between the inner and outer cylindrical sleeves 260, 262. Tuning circuit input leads 270, 272, 274 and a ground lead 276 may be bundled into a cable 278 that extends from the face plate 88*a* to a switching circuit 241*a* located in the power head 90. The switching circuit 241*a* may operate in any appropriate manner, such as in a manner like that previously described with respect to the switching circuit 241*b* of FIG. 14. The switching circuit 241*a* may be controlled by an R/W driver circuit 224*a* that may be located in the power head 90. To exchange data with the data tag 60*a*, the R/W driver circuit 224*a* may execute a communications cycle utilizing the antenna loops 254, 256, 258 in a manner similar to that described with respect to FIG. 15. Thus, in initiating communications with the data tag 60*a*, the R/W RF driver circuit 224*a* may connect the antenna bops 254, 256, 258 in different circuit configurations in order to find a circuit configuration providing the most reliable communications with the data tag 60*a*. By using more than two antenna loops, less power may be required to initiate a communications cycle with the data tag 60*a*. In additional exemplary embodiments, while the antenna system 229*a* is shown as including three antenna loops, other embodiments may include other appropriate quantities and/or arrangements of antenna loops. Further, while the antenna system 229*a* is shown as a component of the pressure jacket 250, other embodiments may include an antenna system having a plurality of antenna loops that is not associated with a pressure jacket.

In its various embodiments, the antenna systems 229*a*, 229*b* may advantageously incorporate one or more antenna loops that can be powered individually, or mutually coupled together, to produce several tuned antenna and EM field configurations. In some environments, the antenna systems 229*a*, 229*b* may be characterized as providing an effective low power system for reading data from and/or writing data to a data tag that may be disposed at any location on a contrast media syringe. Moreover, that contrast media syringe may exhibit virtually any orientation relative to a faceplate of a power injector 50 with which it may be associated. Thus, the antenna systems 229*a*, 229*b* may positively address various challenges relating to use of an RF communications system around metallic or diamagnetic materials, e.g., water, saline, contrast media, or other fluids, and/or in a regulated environment that may mandate use of a relatively low power RF signal.

Figure 1B:
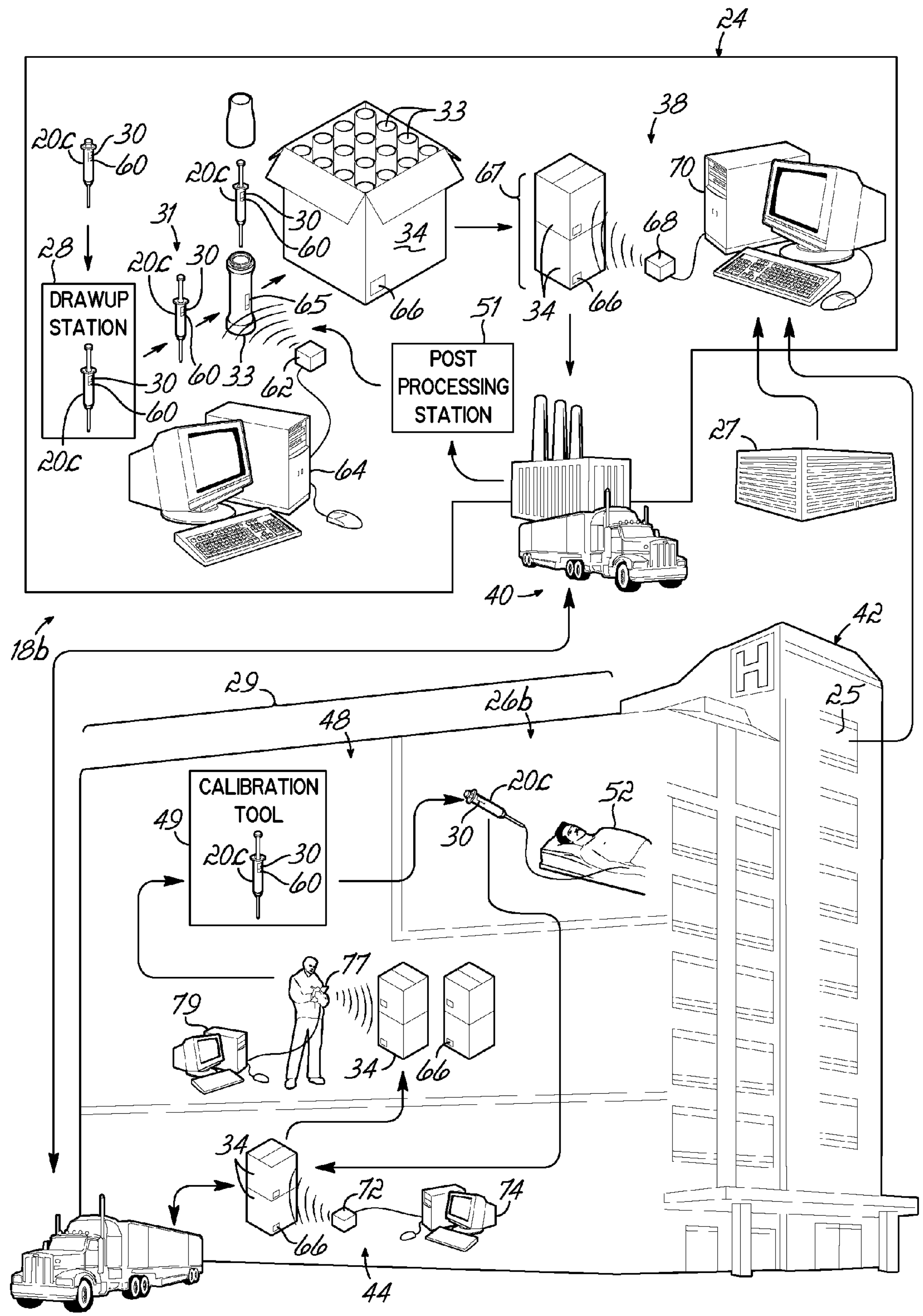
FIG. 1B is a schematic drawing of a system for tracking a container filled with a radiopharmaceutical over a container life cycle.

The exemplary embodiments described with respect to FIG. 1A relate generally to a life cycle of a container 20 such as a syringe filled with a pharmaceutical such as a contrast media. However, referring to FIG. 1B, a container life cycle 18*b* may relate to other types of containers 20*c* that are used to store radiopharmaceuticals. While much of the container life cycle 18*b* of FIG. 1B is generally similar to container life cycle 18*a* of FIG. 1A, radiopharmaceuticals require different handling and storage. The container 20*c* is schematically shown as a syringe, but the container 20*c* may be a vial or other container suitable for use with a radiopharmaceutical. Within the supplier facility 24, after the container 20*c* is filled with a radiopharmaceutical at a drawing-up or filling station 28, a quality control check of the radiopharmaceutical may be performed at quality control station 31. Thereafter, the container 20*c* is placed or loaded into a pig 33, which generally includes lead and/or other radiation shielding material to protect handlers from exposure to radiation from the radiopharmaceutical.

In a manner similar to that described with respect to container 20 of FIG. 1A, as shown in FIG. 1B, the loaded pig 33 may then be packaged either singularly or as a batch in an appropriate shipping carton 34 and shipped to a customer or user. Often, the cartons 34 are stored in a nuclear medicine department 29 within the hospital 42, which generally includes a radiopharmacy 48 and treatment room 26*b*. As required, a radiopharmaceutical container may be removed from a pig and placed in a calibration tool 49 to calibrate an activity level of the radiopharmaceutical to a desired level prior to its use. The radiopharmaceutical container may then be placed back into the pig; and at an appropriate time, the pig may be carried to a treatment room 26*b*. The radiopharmaceutical container may again be removed from the pig, and the radiopharmaceutical may be injected into a patient 52 either manually or using a powered injector such as that shown and described herein. In various embodiments, different manual or powered injectors may utilize various principles of the invention, and are thus, included within the scope of this disclosure.

After use, the radiopharmaceutical container may be placed in the pig and returned to the supplier facility 24; and at a post processing station 51, the radiopharmaceutical container may be disposed of and the pig may be cleaned for reuse.

An exemplary embodiment of a radiopharmaceutical container draw-up and packaging process implemented at a supplier facility 24 is illustrated in FIG. 6. A radiopharmaceutical container 20*c* is filled, at 502, with a radiopharmaceutical at a draw-up station 28. Thereafter, at 504, a label 30 and/or RFID tag 60 are applied to the radiopharmaceutical container 20*c* at the labeling station 32. The RFID tag 60 can be integrated with, or separate from, the label, and the RFID tag 60 incorporates an RFID chip and associated antenna in a known manner.

Figure 18:
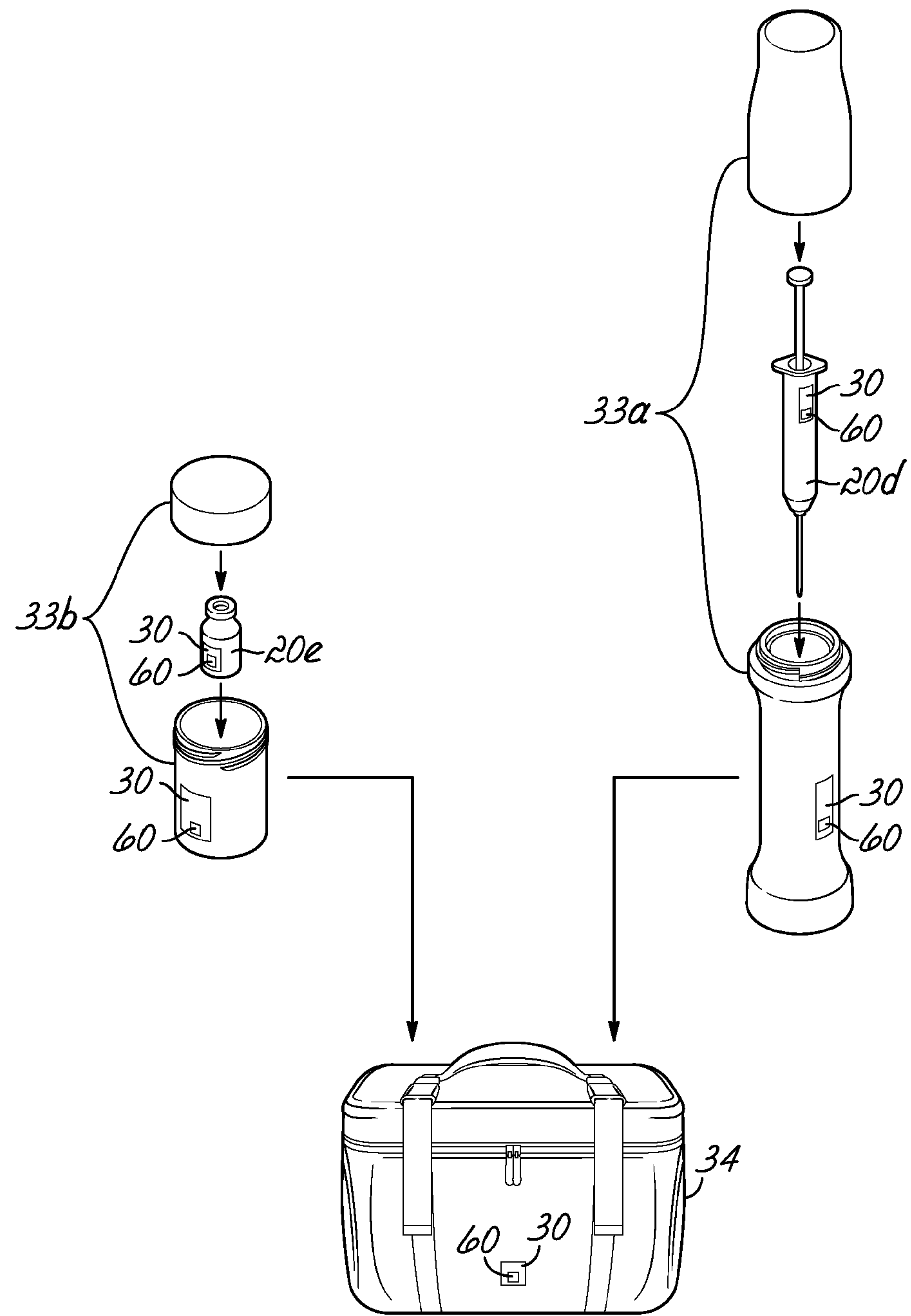
FIG. 18 illustrates different manners of applying a tracking device to a radiopharmaceutical container and respective pig in the system shown in FIG. 1.

As shown in FIG. 18, the RFID tag 60 can be applied at any suitable location on a radiopharmaceutical container. For example, the RFID tag 60 can be part of a label 30 that is applied to a radiopharmaceutical syringe 20*d* or a radiopharmaceutical vial 20*e*. In the example of the radiopharmaceutical syringe 20*d*, an RFID tag can be applied to, or integrated into, the syringe structure at different locations as previously described with respect to FIGS. 2A-2D. In a further embodiment, the syringe label 30 may be removable; and immediately prior to the syringe 20*d* being loaded into a power injector, a portion of the label 30 including the RFID tag can be peeled off and applied to the injector or an associated reader. Upon removing the radiopharmaceutical syringe 20*d* from the injector, the RFID tag 30 is reapplied to the radiopharmaceutical container 20*d*. An identical or different label 30 can also or alternatively be applied to a radiopharmaceutical syringe pig 33*a* or a radiopharmaceutical vial pig 33*b*. Further, a label 30 with an RFID tag 60 can be applied to a carton 34, for example, a satchel, designed to transport a plurality of pigs.

Figure 3B:
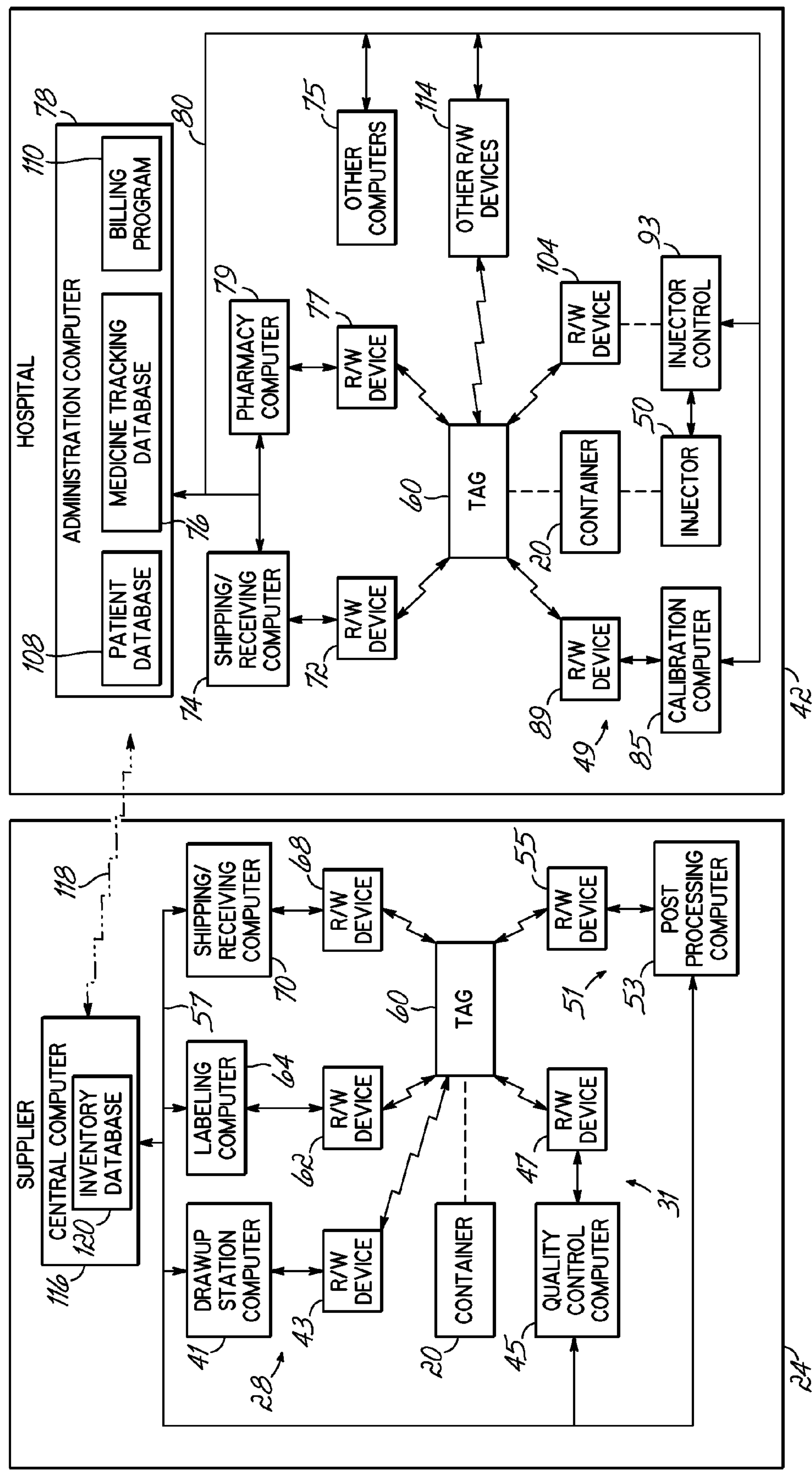
FIG. 3B is a schematic block diagram of components associated with the system illustrated in FIG. 1B.

Within the supplier facility 24 of FIG. 1B, a read/write ("R/W") device 62 is connected to a label computer 64 and, at 506 (FIG. 6), is operative to read data from and/or write data to the RFID tag 60 for a particular radiopharmaceutical container 20*c*. As shown in FIG. 3B, the draw-up station 28 may include a draw-up station computer 41 in electrical communications with an R/W device 43; and depending on the application, either or both of the R/W devices 43, 62 can be used to write data to the RFID tag 60, which data includes but is not limited to the data previously described with respect to step 506. With a radiopharmaceutical, the data may also include all of the dose and prescription information that is currently being printed on a prescription label and/or encoded into a bar code, measured radioactivity levels, for example, Tc-99 and Mo-99, and time when measured, an identity of radioactive elements used, for example, Tc-99 and Mo-99, their respective sources, and other suitable data.

Returning to FIG. 6, processes shown in phantom at 507 and 509 are performed that are unique to the radiopharmaceutical containers 20*c*. First, at 507, quality control checks may be performed (e.g., at a quality control station 31) to determine, for example, a purity of the radiopharmaceutical, the correctness of information on the label, dosage information, etc. As shown in FIG. 3B, the quality control station 31 may include a quality control computer 45 and an associated R/W device 47 that may be used to read data from and/or write data to the RFID tag 60 depending on the quality control checks performed and/or other system specifications.

The container 20*c* may then, at 509, be inserted into a pig 33 for handling, storage and transportation. A label 65 can optionally be applied to the pig 33. The label 65 can include human readable indicia, machine readable indicia and/or an RFID tag as described with respect to the label 30. As part of the process of inserting the container 20*c* into the pig, either the R/W device 62 or another R/W device can be used to read data from and/or write data to the RFID tag 65. Data that can be written to the RFID tag 65 may include data written to the RFID tag 60 on the container 20*c* as well as data that includes, but is not limited to, the following:

A unique identification number for the pig.

An identity of a factory, production line, and/or batch number associated with the pig.

A date and time at which the container was inserted into the pig.

Any other data associated with the order, the radiopharmaceutical, its container 20*c* and associated pig 33.

At 508 in FIG. 6 (in a manner similar to that previously described with respect to FIG. 1A), one or more pigs 33 may be loaded into a shipping carton 34 (see FIG. 1B). At 510, the cartons 34 may be stocked as inventory in a shipping/receiving department 38. Based on orders received, as indicated at 512, the cartons 24 may be further combined or palletized into a case or batch 67 for shipment to a customer; and a label 66 can be optionally applied to an individual shipping carton 34 or a unified case or batch 67 of cartons.

Referring to FIGS. 1B and 7, the cartons 34 may then enter the distribution channel 40 and may be received by a receiving department 44 of a treatment facility such as the hospital 42. A stocking and preparation process may be executed in process steps 602 and 604, which are similar to those previous described. Also in step 606, cartons may be delivered to a hospital radiopharmacy 48 (or nuclear medicine department of a healthcare facility or other appropriate location), and within the radiopharmacy 48, an R/W device 77 connected to a computer 79 can be used to read data from and/or write data to the pig RFID tags 65. As shown in FIG. 3B, the computer 79, via the communications link 80, can also be used to update the medicine tracking database 76 within the hospital administration computer 78.

Processes unique to radiopharmaceutical containers are shown in phantom at 607 and 609 in FIG. 7. Specifically, within the radiopharmacy 48, a calibration tool 49 is often used, at 607, to check or validate a radioactivity level of the dosage of the radiopharmaceutical within a container, This check/validation can be performed using any appropriate process and/or calibration tool. As shown in FIG. 3B, the calibration tool 49 may have a calibration computer 85 connected to an R/W device 89 that, during the check/validation process, can be used to read data from and/or write check/validation data to the container RFID tags 30 and/or the pig RFID tags 65. This check/validation data may include but is not limited to A check/validation time and date.

The decay factor or half life of the radiopharmaceutical.

The prescribed activity level (curie level of radiation) at injection time.

The activity level at another time, for example, the draw-up time.

A measured radioactivity level.

A desired radioactivity level at time of treatment.

An identity of the radioactive element injected.

An identity of the calibration tool and operator, etc.

Continuing in FIG. 7, at the appropriate time, at 609, a pig 33 may be delivered to a treatment room for use. The radiopharmaceutical can be administered manually or using a power injector. In most, but not all cases, a syringe **20*d* or vial 20*e* containing the radiopharmaceutical is removed from a respective pig 33 for manual administration; but in other applications, a power injector and process as previously shown and described with respect to FIG. 8 may be used. With a radiopharmaceutical, the R/W device 104 associated with the injector control 93 (see FIG. 3B) may write the current time and date to the RFID tag 60** to permit tracking of out-of-pig time (e.g., the duration of time that a syringe or vial is not housed within the pig), if desired. During the radiopharmaceutical injection process, the displacement of the radiopharmaceutical container plunger may be precisely controlled, and plunger feed may be tracked (e.g., recorded and written to a tag associated with syringe and/or pig).

It should be noted that labeling systems described herein have potential for eliminating a need for the calibration tool 49. For example, the R/W device 104 of FIG. 3B can read a radioactivity level and time and date of measurement written into the RFID tag by the quality control station 31 (FIG. 1B). Injector control 93 can then calculate the time elapsed between the measured radioactivity level and the scheduled treatment time and date. The injector control 93 can further calculate the decay in radioactivity level over the elapsed time; and then, being programmed with the prescribed radiopharmaceutical dose, the injector control can calculate the correct unit dose volume to be injected. Thus, a calibration tool 49 may not be required. If the radiopharmaceutical is to be injected manually, the computer 79 and associated R/W device 77 can be used by a clinician or other appropriate personnel in a similar fashion to provide a display of the computed current unit dosage without using a calibration tool.

Figure 19:
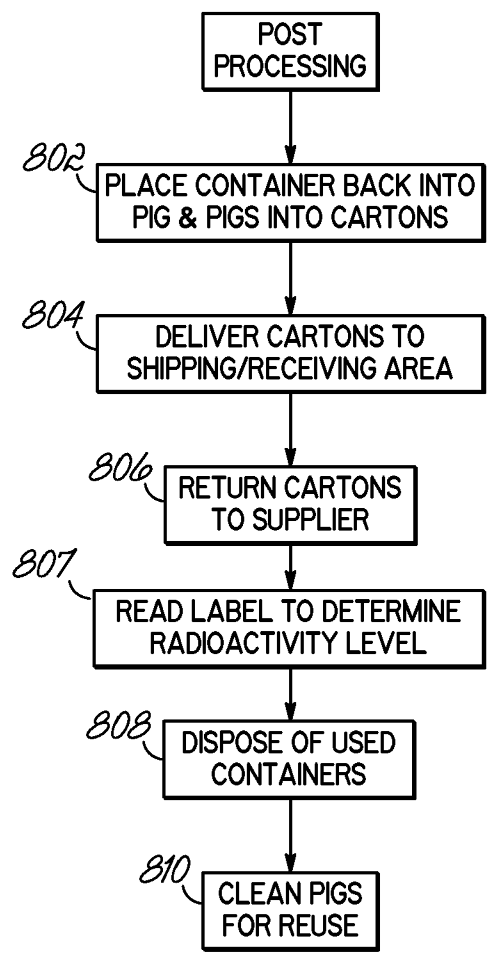
FIG. 19 is a flowchart of an exemplary method of post-processing a radiopharmaceutical container and associated pig.

After the injection process, referring to FIGS. 1B, 5A and 19, the radiopharmaceutical container **20*c* may be removed from the faceplate 88*b* and placed back into a respective pig 33 as indicated at 802 in FIG. 19. The pig 33 may then be placed in the same or a different carton and, at 804, returned to the shipping department 44 and, at 806, returned to the supplier facility 24. As shown in 807**, the label associated with the radiopharmaceutical container may be read just prior to disposal to assist in determining how long the container will have to be stored in a radiation-shielding disposal and/or storage container before substantially all of its radioactivity has decayed. For instance, the initial radioactivity of the radiopharmaceutical may be written to the tag at the time of filling the container. Subsequent to that initial fill time, the radioactivity of that radiopharmaceutical decays. Since the rate of decay is generally known, one may utilize the rate of decay and the duration of time that has passed from the initial fill time to determine how much storage time may be needed to sufficiently ensure that the spent container no longer has a significant amount of radioactivity associated therewith. This calculation of storage time may be accomplished manually and/or electronically (e.g., using an appropriate computer interconnected with the reader utilized to read the tag just prior to disposal).

At post processing station 51 within the supplier facility 24 (FIG. 1B), at 808, the used radiopharmaceutical container may undergo suitable processing for disposal and, at 810, the associated pig may be cleaned for reuse. During post processing, any of the computers previously described can be used to read data from and/or write data to the RFID tags on the container **20*c*, pig 33, carton 34 and/or pallet 67. Such activity may be application dependent to fulfill the needs of a particular supplier, customer, doctor and/or hospital. As shown in FIG. 3B, a post processing computer 53 may be connected to an R/W device 55 that can be used to read data from and/or write data to the RFID tags 60 on one or both the radiopharmaceutical container or the pig. The post processing computer 53 may be able (via a communications link 57) to update a supplier inventory database 120 tracking radiopharmaceutical containers and pigs within the supplier's facilities. The RFID tags 60 on the radiopharmaceutical pigs 33 may be updated or replaced. Further, if desired, data relating to the radiopharmaceutical containers and pigs can be communicated from a supplier computer 116 to computer 79 within the hospital 42 via a communications link 118**, for example, an Internet connection, a telephonic connection, or other suitable link.

In methods as contemplated herein, RF tags 60 may be applied to a radioactive pharmaceutical container **20*c* that is subsequently placed in a lead lined pig 33. In such a circumstance, the pig limits the usability of the RF tags 60 and may prevent use thereof unless the container 20*c* is removed from the pig 33. Therefore, it would be highly desirable to be able to read data from, and write data to, the RF tag 60 on the radiopharmaceutical container 20*c* when it is stored inside the pig 33. Such is achieved by an exemplary embodiment of a pig-mounted antenna system shown in FIGS. 20-22**.

Figures 20, 21:
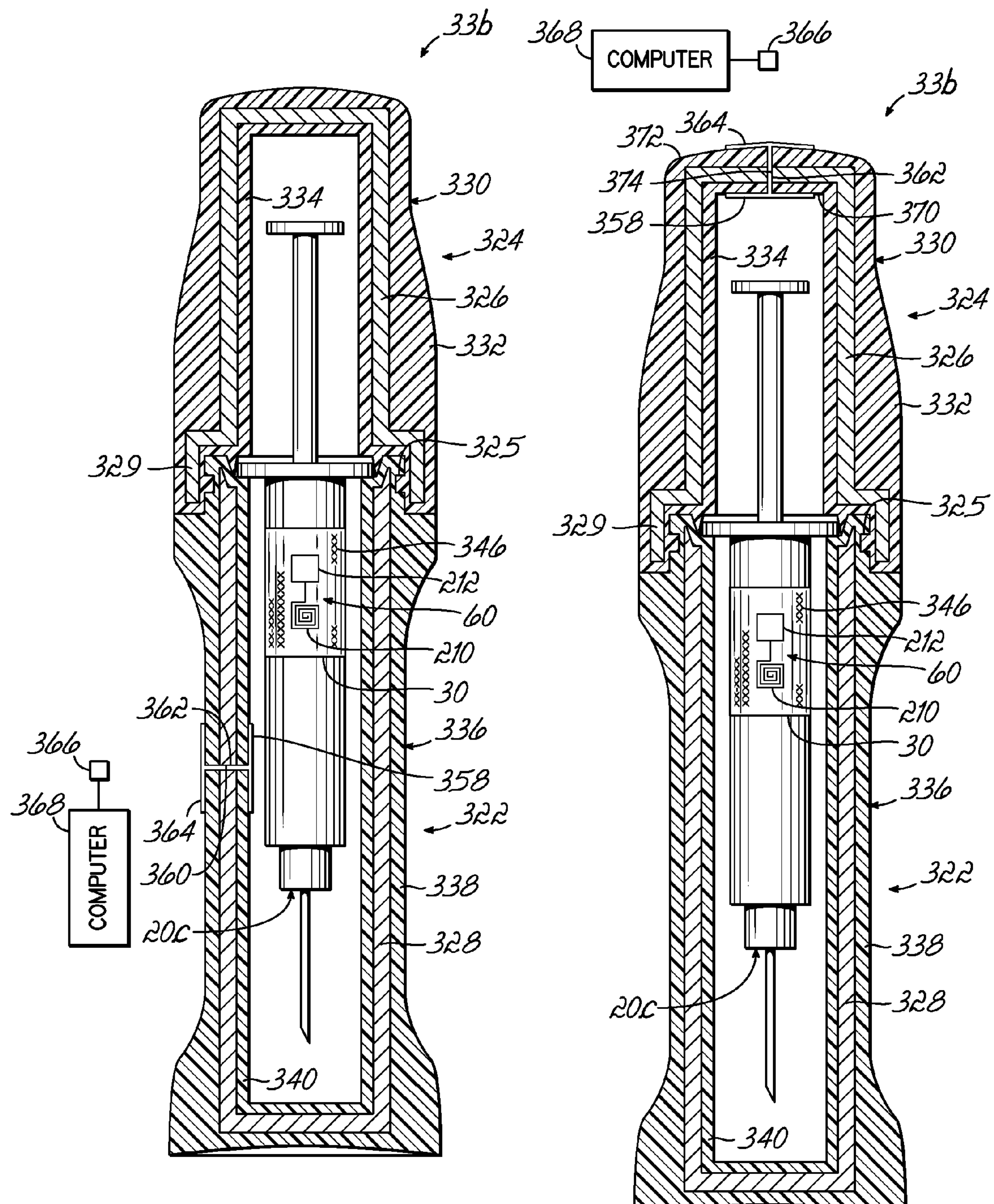
FIG. 20 is a perspective view of an exemplary embodiment of an RF tag and antenna system that is applicable to a radiopharmaceutical syringe and associated radiopharmaceutical pig in accordance with the principles of the present invention.
FIG. 21 is a perspective view of another exemplary embodiment of an RF tag and antenna system that is applicable to a radiopharmaceutical syringe and associated radiopharmaceutical pig in accordance with the principles of the present invention.

Referring to FIG. 20, in a first embodiment, a radiopharmaceutical pig **33*b* has an elongated base 322 and an elongated cap 324. The base 322 and cap 324 can be formed in any of a wide variety of shapes and sizes, however, a substantially cylindrical shape is illustrated. The cap 324 is joined to the base 322 by a threaded interconnection 325 in a known manner. A cap shielding element 326 within the cap 324 and a base shielding element 328 within the base 322 are used to block radiation that may be emitted from the radiopharmaceutical within a syringe 20*c*. The shielding elements 326, 328 can be formed from any material that is effective to block radiation, for example, lead, tungsten, a filled polymer composite material, etc. The cap shielding element 326 forms a protrusion 329 that overlaps the base shielding element 328 when the cap 324 is mounted on the base 322. This overlap of the shields 326, 328 facilitates a blockage of radiation through a discontinuity in the shields caused by the cap 324 being separable from the base 322**.

The cap 324 further has a cap shell 330 comprised of an outer shell portion 332 and an inner shell portion 334. Similarly, the base 322 has a cap shell 336 comprised of an outer shell portion 338 and an inner shell portion 340. The base and cap shells 328, 330 are made from a plastic material, for example, a polycarbonate resin, etc.

A label 30 is affixed to the radiopharmaceutical syringe **22*c* by known means, for example, an adhesive, tape, elastic bands, etc. Indeed, the label 30 may be affixed to the radiopharmaceutical syringe 20*c* in any appropriate manner (e.g., so that it is not easily removable). The label 30 contains indicia 346 that is in human readable and/or machine readable form. The label 30 further has an RFID tag 60 that comprises an RFID integrated circuit chip 212 and at least one radio frequency antenna 210. The radiopharmaceutical syringe 20***c* is often manufactured at a facility independent of the healthcare facility where it is to be used. Therefore, data relating to the radiopharmaceutical syringe 20*c* is often collected at the point of its manufacture. Further, additional data is often collected at different points in a distribution channel at which the radiopharmaceutical pig 33*b* containing the radiopharmaceutical syringe 20*c* is handled. Data is also collected upon the radiopharmaceutical syringe 20*c* being used and thereafter, upon its disposal or cleaning for an authorized reuse. Thus, over the life of the radiopharmaceutical syringe 20*c* and associated radiopharmaceutical pig 33*b*, data that can be written into the RF ID tag 60 at different times in the life cycle of the syringe 20*c* has been previously described. Such data includes but is not limited to the decay factor for a radiopharmaceutical (e.g., half life of pharmaceutical), its prescribed activity level (curie level of radiation) at injection time, the activity level at another time (such as filling time), and/or the time at which the preparing physician or radiopharmacist assumed the radiopharmaceutical would be injected. The activity level is a function of time due to the short half life of most radiopharmaceuticals, so the activity level is designed for a specific injection time.

In order to obtain a maximum benefit from the data stored within the RFID tag 60, it is necessary to be able to read the tag when the radiopharmaceutical syringe 20*c* is housed within the radiopharmaceutical pig 33*b*. In the embodiment of FIG. 20, at least one radio frequency inner antenna 358 is applied over an inner surface of the inner base shell 340; and at least one radio frequency outer antenna 364 is applied over an outer surface of the outer base shell 338. A hole 360 extends through the inner base shell 340, the base shield 328, and the outer base shell 338. At least one connecting lead 362, for example, a copper wire lead, extends through the hole 360 and has one end connected to the inner antenna 358 and an opposite end connected to the outer antenna 364.

The inner antenna 358 is designed to couple with the RFID antenna 210 connected to the RFID chip 212. The outer antenna 364 is designed to electromagnetically couple with a read/write ("R/W") device 366 in the same way that the RFID antenna 210 would couple with the R/W device 366. The R/W device 366 is connected to a computer 368 in a known manner. The R/W device 366 electromagnetically couples with the RFID antenna 210 via the inner and outer antennas 358, 364 respectively. Therefore, any time the radiopharmaceutical pig 33*b* is handled in its life cycle, the R/W device 366 can be used to read information from, and/or write information to, the RFID chip 212 of the RFID tag 60 on the radiopharmaceutical syringe 20*c* via an RFID antenna system comprising the antennas 210, 358, 362, 364. It should be noted that the antenna may simply comprise leads of a sufficient length to be used as an RFID antenna, in which case there may not be a coiled antenna section 364.

Another exemplary embodiment of a radiopharmaceutical pig 33*b* and radiopharmaceutical syringe 20*c* utilizing the RFID tag 60 is shown in FIG. 21. In this embodiment, inner and outer antennas 358, 364 are located on respective inner and outer surfaces 370, 372 of a top of the cap 324. The antennas 358, 364 are electrically connected by at least one lead 362 extending through a hole 374 in the top of the cap 324. The R/W device 366 is able to electromagnetically couple with the RFID antenna 210 via the inner and outer antennas 358, 364 respectively. Therefore, at any time the radiopharmaceutical pig 33*b* is handled in its life cycle, the R/W device 366 can be used to read information from, and/or write information to, the RFID chip 212 of the RFID tag 60 on the radiopharmaceutical syringe 20*c* via an RFID antenna system comprising the antennas 210, 358, 364.

Placing the antennas 358, 362 in the top of the cap 324 has some advantages. First, the top of the cap 324 often experiences less radiation exposure than the base shell 336. Further, the cap outer surface 372 often experiences less physical contact than the base outer shell 338 during the handling of the radiopharmaceutical pig 33*b*; and hence, the outer antenna 362 on the cap outer surface 372 is less subject to physical damage.

Figure 22:
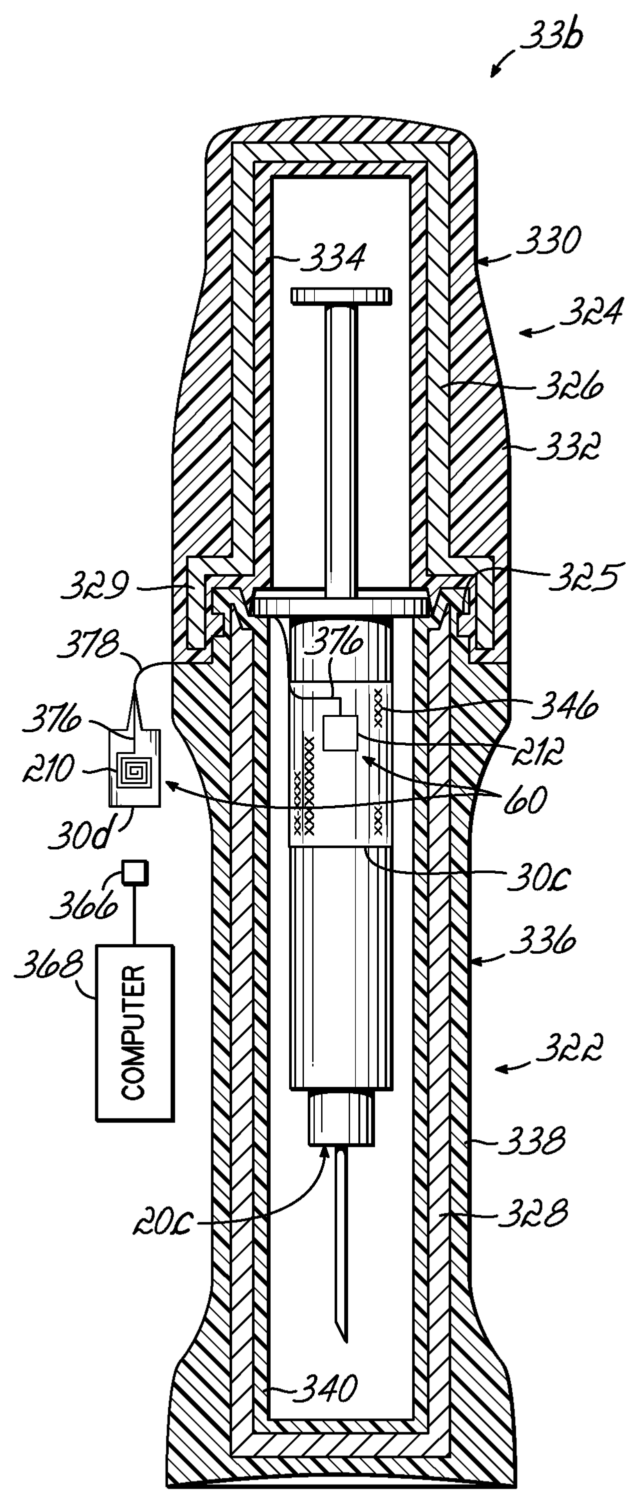
FIG. 22 is a perspective view of a further exemplary embodiment of an RF tag and antenna system that is applicable to a radiopharmaceutical syringe and associated radiopharmaceutical pig in accordance with the principles of the present invention.
Figure 22A:
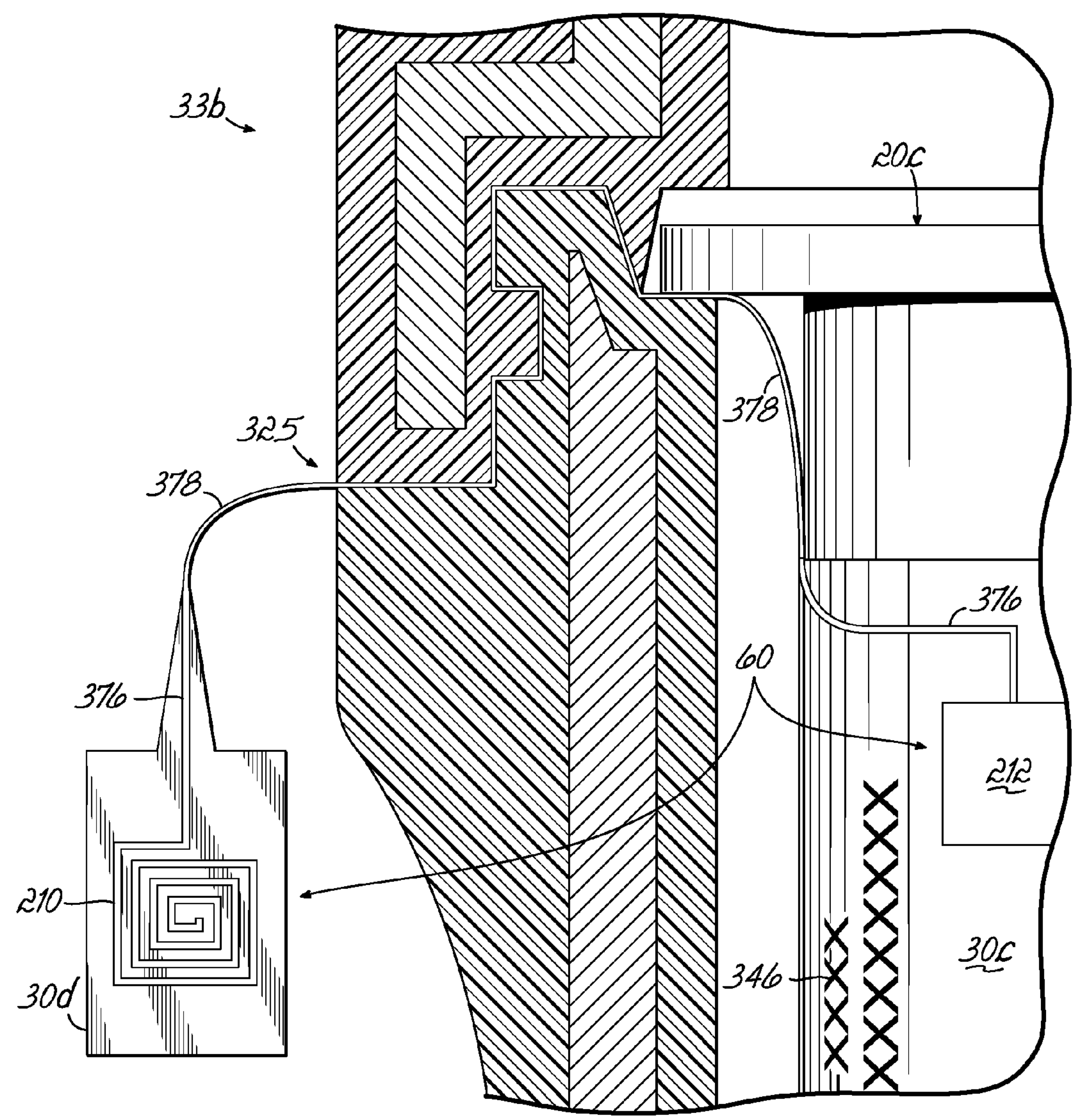
FIG. 22A is an exploded view showing a path of an antenna lead in the further embodiment of the radiopharmaceutical syringe and associated radiopharmaceutical pig shown in FIG. 22.

A further exemplary embodiment of a radiopharmaceutical pig 33*b* and radiopharmaceutical syringe 20*c* utilizing an RFID tag 60 is shown in FIGS. 22 and 22A. In this embodiment, the RFID tag 60 has an RFID chip 212 on a first portion of a label 30*c* that is attached to the radiopharmaceutical syringe 20*c* in a manner described earlier with respect to FIG. 20. A second portion of the label 30*d* is located outside of the radiopharmaceutical pig 33*b* and has at least one RFID antenna 210 thereon. The RFID chip 212 on the first label portion 30*c* is electrically connected to the antenna 210 by at least one electrically conductive lead 376 integral with a tether 378. The conductive lead 376 and tether 378 may be formed from any materials that provide the desired electrical and mechanical properties, for example, an insulated or uninsulated copper wire, a copper trace laminated on a substrate, etc. The threaded connector 325 is designed to provide a clearance for the conductive lead 376 and tether 378, so that the cap 324 can be attached and removed from the base 322 without damaging the conductive lead 376 and tether 378. The R/W device 366 is able to electromagnetically couple with the RFID antenna 210, and the RFID antenna 210 communicates data to and from the RFID chip 212 via the conductive lead 376. Therefore, at any time the radiopharmaceutical pig 33*b* is handled in its life cycle, the R/W device 366 can be used to read information from, and/or write information to, the RFID chip 212 of the RFID tag 60 on the radiopharmaceutical syringe 20*c* via an RFID antenna system comprising the antenna 210 and conductive lead 376.

In use, upon receiving an order for a radiopharmaceutical, a label 30 having an RFID chip 212 and associated antenna 210 is applied to the radiopharmaceutical syringe 20*c*, and the radiopharmaceutical syringe 20*c* can be placed in a radiopharmaceutical pig 33*b*. At that time, data including but not limited to the identity of the syringe and pig can be written to the RFID tag 60 in a manner previously described with respect to FIGS. 1A and 1B. The radiopharmaceutical syringe 20*c* and pig 33*b* are then transported to a location where the syringe 20*c* is filled with a desired radiopharmaceutical. This location may be at a radiopharmaceutical supplier or a location of a user of the radiopharmaceutical syringe 20*c*. In either event, regardless of where the radiopharmaceutical syringe 20*c* is filled, as previously described, data can be entered into the RFID tag 60 relating to the filling process, the radiopharmaceutical being filled, and the how the radiopharmaceutical is to be used. After being filled, the pig 33*b* holding the syringe 20*c* filled with the radiopharmaceutical may be transported and stored several times before it is delivered for use in a preparation and/or imaging room. During use, the syringe 20*c* is removed from the pig 33*b*, and the radiopharmaceutical is injected into an examination subject or patient. After use, the empty syringe 20*c* is placed back in the pig 33*b* and returned to the pharmaceutical supplier or other location for proper disposal of the radiopharmaceutical syringe 20*c* and reconditioning of the radiopharmaceutical pig 33*b* for reuse.

Every time the radiopharmaceutical pig 33*b* and/or radiopharmaceutical syringe 20*c* is handled over their respective life cycles, in a manner as previously described, an R/W device 366 can be used to read data from, and/or write data to, the RFID tag 60, thereby providing complete chronological history of the radiopharmaceutical pig 33*b* and syringe radiopharmaceutical 20*c* over the respective life cycles. The systems illustrated in FIGS. 1A, 3A, 1B, 3B have an advantage in that almost any information is able to be transferred between all entities involved in a life cycle of a syringe 20, which is any entity that can communicate with the communication link 80. Therefore, data available from a website on the internet 83 can be utilized during the life cycle of the syringe 20. Such internet communications capabilities permits remote service of a power injector 50, downloading of an injection protocol, communication with a remotely located physician, media supplier or other entity of interest and other functions.

While the various principles of the invention have been illustrated by way of describing various exemplary embodiments, and while such embodiments have been described in considerable detail, there is no intention to restrict, or in any way limit, the scope of the appended claims to such detail. Additional advantages and modifications will readily appear to those skilled in the art. For example, in the described embodiments of FIGS. 20-22, an RFID chip 212 may be positioned inside the pig. In some embodiments, the chip 212 may be located outside the pig along with an associated antenna, and the chip may be physically attached to the syringe 20*c* by a string or other attachment so that the radiopharmaceutical syringe 20*c* and RFID information therein remain associated. Alternatively, the pig 33*b* may carry an RFID tag and antenna with no mechanical attachment to the syringe, but it may simply be known that the data therein relates to the syringe that is in the pig.

Further, in the exemplary embodiments shown and described herein, the antenna systems 229*a*, 229*b* use one, two and three antenna loops; however, in alternative embodiments, any number of antenna loops may be used. The antenna loops may be configured in any shape and be in the same plane or in different planes. Further, the antenna loops may or may not be overlapping. In may, however, be preferable that the antenna loops be individually tuned to resonate at a specific frequency used by the RFID protocol. Further, in the described embodiment, a switching circuit 241*b* is located on the same PC board 102 as an RF driver circuit 224*b*; however, in alternative embodiments, a switching circuit may be located on the second PC board 103, be split between the two PC boards 102, 103 or located elsewhere, for example, with the power injector as shown in FIG. 17.

In addition, in the described embodiments, the R/W antenna systems 229*a*, 229*b* are applied to a pharmaceutical injection assembly; however, in alternative embodiments, the R/W antenna systems 229*a*, 229*b* utilizing multiple nonparallel antennas may be applied to any devices that support a medical fluid container. Such devices include but are not limited to a warmer oven or warming box, a container filling station, a pig or other nuclear medicine container, a dose calibration station, a handheld powered medical fluid dispenser, a syringe disposal station, or other device.

Figure 1C:
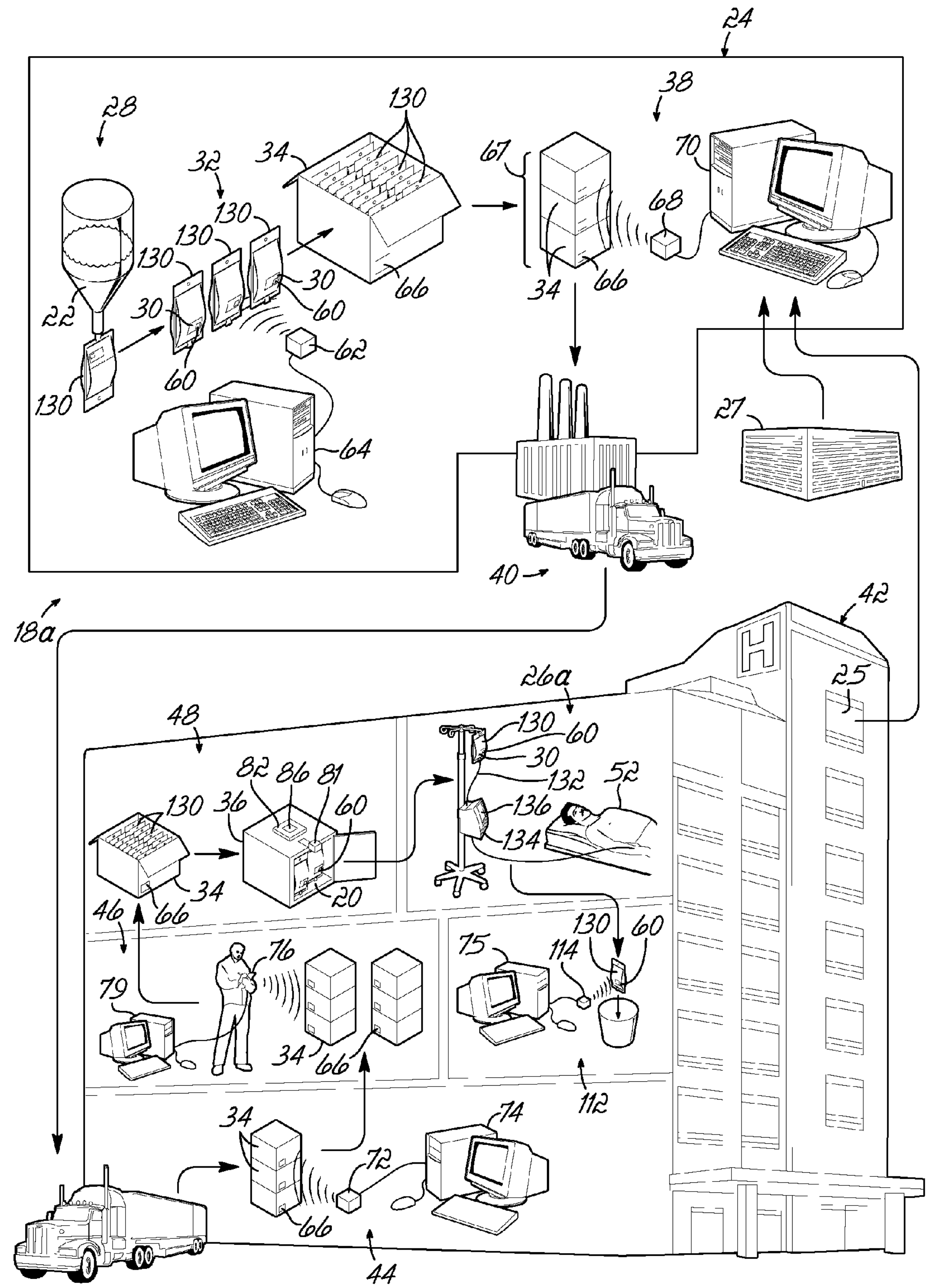
FIG. 1C is a schematic drawing of a system for tracking an IV bag filled with a medical fluid over an IV bag life cycle.
Figure 3C:
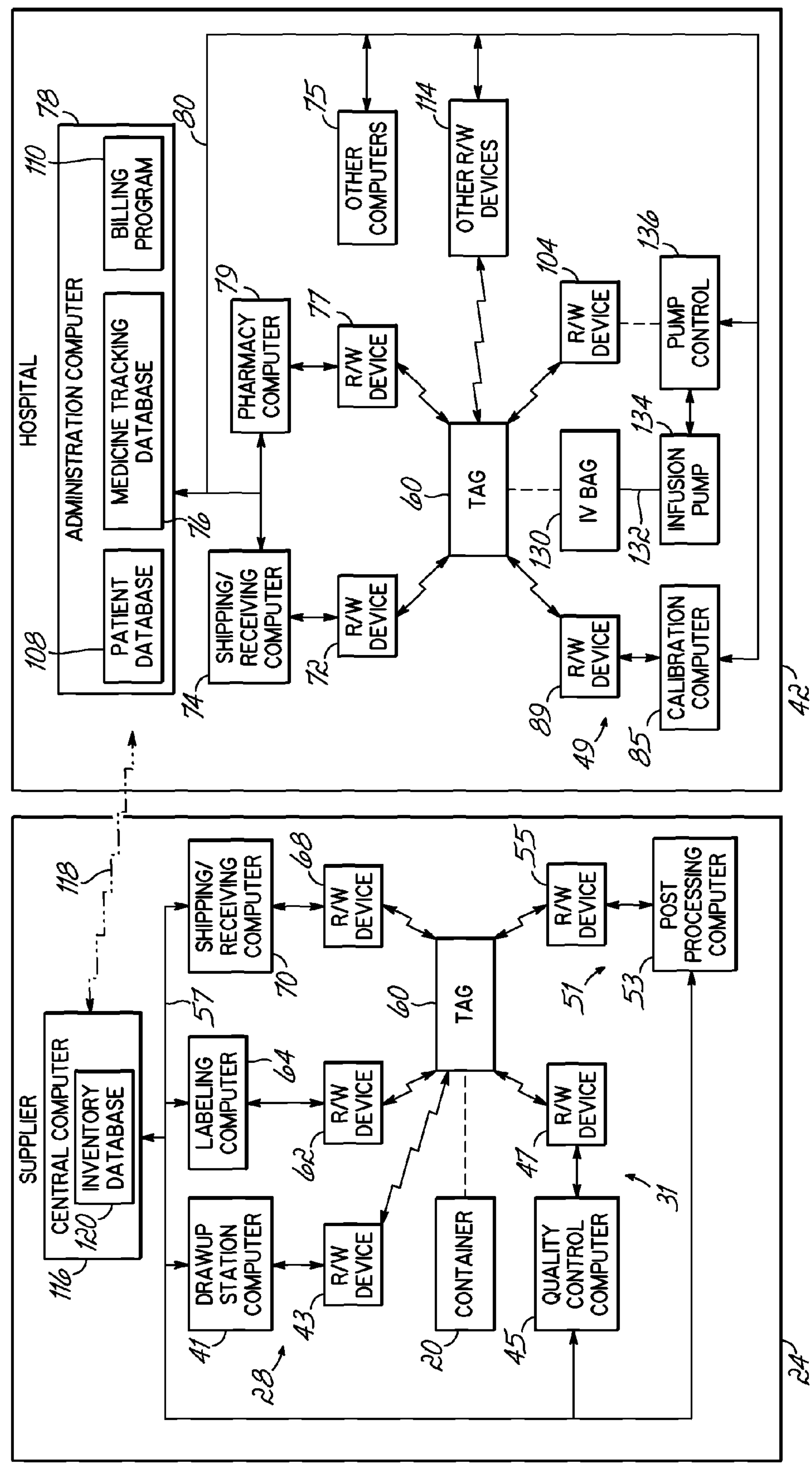
FIG. 3C is a schematic block diagram of components associated with the system illustrated in FIG. 1C.

The systems of the described embodiments relate to containers of medical fluids. Two examples described in detail relate to contrast media and respective syringes and radiopharmaceuticals and respective containers. In alternative embodiments, referring to FIG. 1C, the container may be an IV bag 130 filled with a medical fluid. Tubing 132 from the IV bag 130 may interface with an infusion pump 134 so that a flow of medical fluid from the IV bag 130 may be regulated via use of the pump 134. While one end of the tubing 132 is generally associated with the IV bag 130, the other end of the tubing 132 may be connected to a patient in a known manner. The IV bag 130 may have a label 30 with a data tag 60 as previously described herein, for example, an RFID tag. Further, the infusion pump 134 may be in electrical communication with an electromagnetic device capable of reading data from and/or writing data to the data tag 60 of the IV bag 130. For example, the electromagnetic device may be attached to and/or located within the infusion pump 134. As shown in FIG. 3C, the infusion pump 134 may have a control 136 connected to the communications link 80 in a manner similar to that described with respect to the injector control 93 shown in FIGS. 1A and 1B. Thus, the systems of FIGS. 1C and 3C may permit activity relating to the IV bag 130, the medical fluid therein, and/or the infusion pump 134 to be tracked and recorded (e.g., over a life cycle of the IV bag 130).

There are many known structures for mounting a syringe to a power injector, and the faceplates shown and described herein are only two such structures. Other mounting structures may not permit removal from the power head. The inventions claimed herein are can be applied to power heads having any type of structure for mounting a syringe thereto. In the shown and described embodiment, a heater 106 is mounted on the PC boards 102, 103; however, in alternative embodiments, the heater 106 may not be used and therefore, deleted from PC boards 102, 103.

When introducing elements of the present invention or various embodiments thereof, the articles "a", "an", "the", and "said" are intended to mean that there are one or more of the elements. The terms "comprising", "including", and "having" are intended to be inclusive and mean that there may be additional elements other than the listed elements. Moreover, the use of "top" and "bottom", "front" and "rear", "above" and "below" and variations of these and other terms of orientation is made for convenience, but does not require any particular orientation of the components.

Therefore, the invention, in its broadest aspects, is not limited to the specific details shown and described herein. Consequently, departures may be made from the details described herein without departing from the spirit and scope of the claims, which follow.

What is claimed is:

1. A method of operation for a contrast media injector having a powered drive ram that is designed to interface with a plunger of a syringe to move the plunger of the syringe forward and backward relative to a barrel of the syringe when the syringe is mounted on the contrast media injector, the method comprising:

detecting when a syringe, having an RF data tag associated therewith, has been mounted on to the contrast media injector;

initiating a transmission of electromagnetic signals from an electromagnetic device of the contrast media injector in response to detection of the syringe being mounted on to the contrast media injector; and electromagnetically reading data generated from the RF data tag of the syringe in response to the transmitted electromagnetic signals.

2. The method of claim 1, wherein the data that is electromagnetically read comprises at least one of: a syringe identification; a serial number; a use indicator of the syringe; a syringe security code; information relating to syringe volume; information relating to syringe volume delivery; syringe volume; syringe dimension information; medical fluid type; medical fluid concentration data; batch and lot numbers; shelf life data; fill date; and combinations thereof.

3. The method of claim 1, wherein the initiating a transmission occurs substantially simultaneously with the syringe being mounted on to the contrast media injector.

4. The method of claim 1, wherein the contrast media injector comprises a latch for securing the syringe that is being mounted on to the contrast media injector, and wherein the initiating a transmission occurs in response to the latch securing the syringe being mounted on to the contrast media injector.

5. The method of claim 4, wherein the initiating a transmission occurs substantially simultaneously with the latch securing the syringe being mounted on to the contrast media injector.

6. A method of operation for a contrast media injector having a powered drive ram that is designed to interface with a plunger of a syringe to move the plunger of the syringe forward and backward relative to a barrel of the syringe when the syringe is mounted on the contrast media injector, the method comprising:

initiating dispensing medical fluid from a syringe having an RF data tag associated therewith, wherein the dispensing is accomplished using the contrast media injector;

transmitting electromagnetic signals from an electromagnetic device of the contrast media injector in response to initiation of the dispensing; and electromagnetically writing data to the RF data tag of the syringe using the electromagnetic device of the contrast media injector.

7. The method of claim 6, wherein the data that is electromagnetically written to the RF data tag comprises at least one of: time that the dispensing was finished; date that the dispensing was finished; dispensed volume; achieved flow rate; target flow rate; volume of medical fluid remaining in the syringe; dispensing time; patient name; patient weight; patient age; patient ID number; injector serial number; injector firmware version; procedure number; procedure name; technologist name; technologist identification number; hospital name; hospital identification number; imaging apparatus information; and combinations thereof.

8. The method of claim 6, wherein initiation of the transmitting occurs substantially simultaneously with the initiation of the dispensing.

9. A method of operation for a contrast media injector having a powered drive ram that is designed to interface with a plunger of a syringe to move the plunger of the syringe forward and backward relative to a barrel of the syringe when the syringe is mounted on the contrast media injector, the method comprising:

detecting when a syringe, having an RF data tag associated therewith, has been mounted on to the contrast media injector;

transmitting electromagnetic signals from an electromagnetic device of the contrast media injector in response to detection of the syringe being mounted on to the contrast media injector;

electromagnetically reading data from the RF data tag of the syringe using the electromagnetic device of the contrast media injector, wherein the transmitting is terminated after the electromagnetically reading;

initiating dispensing medical fluid from the syringe;

transmitting electromagnetic signals from the electromagnetic device in response to initiation of the dispensing; and electromagnetically writing data to the RF data tag of the syringe using the electromagnetic device of the contrast media injector.

10. The method of claim 1, wherein the data that is electromagnetically read includes a use indicator of the syringe.

11. The method of claim 1, wherein the data that is electromagnetically read includes information relating to syringe volume.

12. The method of claim 1, wherein the data that is electromagnetically read includes information relating to syringe volume delivery.

13. The method of claim 1, wherein the data that is electromagnetically read includes a syringe volume.

14. The method of claim 1, wherein the data that is electromagnetically read includes syringe dimension information.

15. The method of claim 1, wherein the data that is electromagnetically read includes a medical fluid type.

16. The method of claim 1, wherein the data that is electromagnetically read includes medical fluid concentration data.

17. The method of claim 1, wherein the data that is electromagnetically read includes batch and lot numbers.

18. The method of claim 1, wherein the data that is electromagnetically read includes shelf life data.

19. The method of claim 1, wherein the data that is electromagnetically read includes a fill date.

20. The method of claim 6, wherein the data that is electromagnetically written to the RF data tag includes a time that the dispensing was finished.

21. The method of claim 6, wherein the data that is electromagnetically written to the RF data tag includes a date that the dispensing was finished.

22. The method of claim 6, wherein the data that is electromagnetically written to the RF data tag includes a dispensed volume.

23. The method of claim 6, wherein the data that is electromagnetically written to the RF data tag includes an achieved flow rate, a target flow rate, and combinations thereof.

24. The method of claim 6, wherein the data that is electromagnetically written to the RF data tag includes a volume of medical fluid remaining in the syringe.

25. The method of claim 6, wherein the data that is electromagnetically written to the RF data tag includes a dispensing time.

26. The method of claim 6, wherein the data that is electromagnetically written to the RF data tag includes a patient name, a patient age, a patient ID number, and combinations thereof.

27. The method of claim 6, wherein the data that is electromagnetically written to the RF data tag includes an injector serial number, an injector firmware version, and combinations thereof.

28. The method of claim 6, wherein the data that is electromagnetically written to the RF data tag includes a procedure number, a procedure name, and combinations thereof.

29. The method of claim 6, wherein the data that is electromagnetically written to the RF data tag includes a technologist name, a technologist identification number, and combinations thereof.

30. The method of claim 6, wherein the data that is electromagnetically written to the RF data tag includes a hospital name, a hospital identification number, and combinations thereof.

31. The method of claim 6, wherein the data that is electromagnetically written to the RF data tag includes imaging apparatus information.

32. The method of claim 1, wherein the mounting of a syringe is detected using a sensor coupled to a syringe mounting.

33. The method of claim 9, wherein the mounting of a syringe is detected using a sensor coupled to a syringe mounting.

* * * * *